(12) United States Patent
Berzin et al.

(10) Patent No.: US 7,980,024 B2
(45) Date of Patent: Jul. 19, 2011

(54) PHOTOBIOREACTOR SYSTEMS POSITIONED ON BODIES OF WATER

(75) Inventors: Isaac Berzin, Jerusalem (IL); Javier de Luis, Cambridge, MA (US); David Fair, Winchester, MA (US); Joe Parrish, Cambridge, MA (US); Keith Richtman, Boston, MA (US); Fan Chen, Santa Clara, CA (US); Benjamin F. Polito, Lebanon, NH (US); Miles Walker, Somerville, MA (US); Ben Fowler, Somerville, MA (US); Kevin Lockwood, Millville, MA (US); Miguel Olaizola, San Diego, CA (US)

(73) Assignee: Algae Systems, Inc., Chicago, IL (US)

(*) Notice: Subject to any disclaimer, the term of this patent is extended or adjusted under 35 U.S.C. 154(b) by 485 days.

(21) Appl. No.: 12/110,178

(22) Filed: Apr. 25, 2008
(Under 37 CFR 1.47)

(65) Prior Publication Data
US 2009/0130706 A1    May 21, 2009

Related U.S. Application Data

(60) Provisional application No. 60/926,622, filed on Apr. 27, 2007, provisional application No. 60/926,569, filed on Apr. 27, 2007.

(51) Int. Cl.
*A01G 7/00* (2006.01)
*C12M 1/00* (2006.01)
(52) U.S. Cl. ............... 47/1.4; 435/289.1; 435/292.1
(58) Field of Classification Search .......... 47/1.4; 435/289.1, 292.1
See application file for complete search history.

(56) References Cited

U.S. PATENT DOCUMENTS

| 1,995,970 A | 3/1935 | Dorough |
| 2,703,316 A | 3/1955 | Schneider |

(Continued)

FOREIGN PATENT DOCUMENTS

| AT | 154828 T | 7/1997 |

(Continued)

OTHER PUBLICATIONS

U.S. Appl. No. 11/632,541, Isaac Berzin, Photobioreactor Cell Culture Systems, Methods for Preconditioning Photosynthetic Organisms, and Cultures of Photosynthetic Organisms Produced Thereby, filed Mar. 14, 2008.

(Continued)

*Primary Examiner* — Robert J Warden
(74) *Attorney, Agent, or Firm* — Peters Verny, LLP

(57) ABSTRACT

Certain embodiments and aspects of the present invention relate to a photobioreactor including photobioreactor units through which a liquid medium stream and a gas stream flow. The photobioreactor units are floated on a body of water such as a pond or a lake. The liquid medium comprises at least one species of phototrophic organism therein. Certain methods of using the photobioreactor system as part of fuel generation system and/or a gas-treatment process or system at least partially remove certain undesirable pollutants from a gas stream. In certain embodiments, the photobioreactor units are formed of flexible, deformable material and are configured to provide a substantially constant thickness of liquid medium. In certain embodiments, a barrier between the photobioreactor unit and the body of water upon which the unit is floated facilitates thermal communication between the liquid medium and the body of water.

17 Claims, 14 Drawing Sheets

U.S. PATENT DOCUMENTS

| | | |
|---|---|---|
| 2,732,663 A | 1/1956 | Dewey, II |
| 2,807,912 A | 10/1957 | Bjorksten |
| 2,854,792 A | 10/1958 | Juda |
| 3,420,737 A | 1/1969 | Bongers et al. |
| 3,420,739 A | 1/1969 | Bongers et al. |
| 3,456,928 A | 7/1969 | Selway |
| 3,468,057 A | 9/1969 | Buisson et al. |
| 3,492,789 A | 2/1970 | Jueng |
| 3,579,907 A | 5/1971 | Graves |
| 3,592,631 A | 7/1971 | Cattelain |
| 3,650,068 A | 3/1972 | Meyer et al. |
| 3,954,615 A | 5/1976 | Shelef |
| 3,954,921 A | 5/1976 | Yoshida et al. |
| 3,955,317 A * | 5/1976 | Gudin ............................ 435/420 |
| 3,998,186 A | 12/1976 | Hodges |
| 4,005,015 A | 1/1977 | Boward, Jr. |
| 4,044,500 A | 8/1977 | Hitzman |
| 4,169,050 A * | 9/1979 | Serfling et al. ................ 210/602 |
| 4,209,943 A | 7/1980 | Moeller et al. |
| 4,217,728 A | 8/1980 | Shimamatsu et al. |
| 4,233,958 A | 11/1980 | Heden |
| 4,253,271 A | 3/1981 | Raymond |
| 4,341,038 A | 7/1982 | Bloch et al. |
| 4,442,211 A | 4/1984 | Greenbaum |
| 4,446,236 A | 5/1984 | Clyde |
| 4,473,970 A | 10/1984 | Hills |
| 4,532,210 A | 7/1985 | Miura et al. |
| 4,577,110 A | 3/1986 | MacBride |
| 4,653,223 A | 3/1987 | Mori |
| 4,658,757 A | 4/1987 | Cook |
| 4,666,852 A | 5/1987 | Cork |
| 4,676,956 A | 6/1987 | Mori |
| 4,786,598 A | 11/1988 | Lafferty et al. |
| 4,828,768 A | 5/1989 | Talmor |
| 4,868,123 A | 9/1989 | Berson et al. |
| 4,888,912 A * | 12/1989 | Murray ............................ 47/1.4 |
| 4,963,486 A | 10/1990 | Hang |
| 4,999,302 A | 3/1991 | Kahler et al. |
| 5,104,589 A | 4/1992 | Palmer et al. |
| 5,137,828 A | 8/1992 | Robinson et al. |
| 5,142,023 A | 8/1992 | Gruber et al. |
| 5,151,347 A | 9/1992 | Delente et al. |
| 5,162,051 A | 11/1992 | Hoeksema |
| 5,213,976 A | 5/1993 | Blauhut et al. |
| 5,216,976 A | 6/1993 | Marinkovich |
| 5,242,827 A | 9/1993 | Chaumont et al. |
| 5,247,058 A | 9/1993 | Gruber et al. |
| 5,247,059 A | 9/1993 | Gruber et al. |
| 5,250,427 A | 10/1993 | Weaver et al. |
| 5,258,488 A | 11/1993 | Gruber et al. |
| 5,269,819 A | 12/1993 | Porath |
| 5,274,073 A | 12/1993 | Gruber et al. |
| 5,310,865 A | 5/1994 | Enomoto et al. |
| 5,330,639 A | 7/1994 | Murphree |
| 5,338,673 A | 8/1994 | Thepenier et al. |
| 5,344,557 A | 9/1994 | Scanzillo |
| 5,357,035 A | 10/1994 | Gruber et al. |
| 5,359,026 A | 10/1994 | Gruber |
| 5,424,209 A | 6/1995 | Kearney |
| 5,440,008 A | 8/1995 | Ichikawa et al. |
| 5,443,985 A | 8/1995 | Lu et al. |
| 5,444,143 A | 8/1995 | Ohta et al. |
| 5,447,629 A | 9/1995 | Chaumont et al. |
| 5,496,923 A | 3/1996 | Suizu et al. |
| 5,510,526 A | 4/1996 | Baniel et al. |
| 5,512,653 A | 4/1996 | Ohta et al. |
| 5,528,856 A | 6/1996 | Smith et al. |
| 5,534,417 A | 7/1996 | Arad et al. |
| 5,541,056 A | 7/1996 | Huntley et al. |
| 5,554,291 A | 9/1996 | Scanzillo |
| 5,591,341 A | 1/1997 | Jensen |
| 5,594,095 A | 1/1997 | Gruber et al. |
| 5,606,170 A | 2/1997 | Saaski et al. |
| 5,612,188 A | 3/1997 | Shuler et al. |
| 5,614,378 A | 3/1997 | Yang et al. |
| 5,628,311 A | 5/1997 | Mauze |
| 5,636,472 A | 6/1997 | Spira et al. |
| 5,659,977 A | 8/1997 | Jensen et al. |
| 5,661,017 A | 8/1997 | Dunahay et al. |
| 5,670,046 A | 9/1997 | Kimmel |
| 5,679,767 A | 10/1997 | Suizu et al. |
| 5,686,276 A | 11/1997 | Laffend et al. |
| 5,691,424 A | 11/1997 | Suzuki et al. |
| 5,714,573 A | 2/1998 | Randall et al. |
| 5,741,702 A | 4/1998 | Lorenz |
| 5,766,474 A | 6/1998 | Smith et al. |
| 5,770,683 A | 6/1998 | Yoshida et al. |
| 5,780,678 A | 7/1998 | Baniel et al. |
| 5,786,185 A | 7/1998 | Tsao et al. |
| 5,798,435 A | 8/1998 | Gruber et al. |
| 5,846,816 A | 12/1998 | Forth |
| 5,882,849 A | 3/1999 | Leonard et al. |
| 5,892,109 A | 4/1999 | Baniel et al. |
| 5,910,254 A | 6/1999 | Guelcher et al. |
| 5,917,010 A | 6/1999 | Goto et al. |
| 5,922,832 A | 7/1999 | Randall et al. |
| 5,942,597 A | 8/1999 | Noda et al. |
| 5,958,761 A | 9/1999 | Yogev et al. |
| 5,981,271 A | 11/1999 | Doucha et al. |
| 5,998,552 A | 12/1999 | Gruber et al. |
| 6,005,067 A | 12/1999 | Gruber et al. |
| 6,022,701 A | 2/2000 | Boussiba et al. |
| 6,025,184 A | 2/2000 | Laffend et al. |
| 6,037,170 A | 3/2000 | Sekine |
| 6,051,437 A | 4/2000 | Luo et al. |
| 6,083,740 A | 7/2000 | Kodo et al. |
| 6,087,532 A | 7/2000 | Baniel et al. |
| 6,111,137 A | 8/2000 | Suizu et al. |
| 6,140,458 A | 10/2000 | Terado et al. |
| 6,156,561 A | 12/2000 | Kodo et al. |
| 6,174,720 B1 | 1/2001 | Oxley et al. |
| 6,187,951 B1 | 2/2001 | Baniel et al. |
| 6,218,173 B1 | 4/2001 | Naito |
| 6,229,046 B1 | 5/2001 | Eyal et al. |
| 6,277,951 B1 | 8/2001 | Gruber et al. |
| 6,285,807 B1 | 9/2001 | Walt et al. |
| 6,291,597 B1 | 9/2001 | Gruber et al. |
| 6,320,077 B1 | 11/2001 | Eyal et al. |
| 6,326,458 B1 | 12/2001 | Gruber et al. |
| 6,348,347 B1 | 2/2002 | Hirabayashi et al. |
| 6,370,815 B1 | 4/2002 | Skill et al. |
| 6,416,993 B1 | 7/2002 | Wexler et al. |
| 6,417,266 B1 | 7/2002 | Terado et al. |
| 6,428,767 B1 | 8/2002 | Burch et al. |
| 6,429,280 B1 | 8/2002 | Hiraoka et al. |
| 6,465,240 B1 | 10/2002 | Wexler et al. |
| 6,472,559 B2 | 10/2002 | Baniel et al. |
| 6,475,759 B1 | 11/2002 | Carlson et al. |
| 6,485,947 B1 | 11/2002 | Rajgarhia et al. |
| 6,492,149 B1 | 12/2002 | Muller-Feuga |
| 6,495,631 B1 | 12/2002 | Randall et al. |
| 6,509,188 B1 | 1/2003 | Trosch et al. |
| 6,534,679 B2 | 3/2003 | Eyal et al. |
| 6,575,714 B2 | 6/2003 | Pace et al. |
| 6,579,714 B1 | 6/2003 | Hirabayashi et al. |
| 6,602,703 B2 | 8/2003 | Dutil |
| 6,603,069 B1 | 8/2003 | Muhs et al. |
| 6,616,845 B2 | 9/2003 | Shechter et al. |
| 6,648,949 B1 | 11/2003 | Der et al. |
| 6,667,171 B2 | 12/2003 | Bayless et al. |
| 6,673,532 B2 | 1/2004 | Rao |
| 6,706,963 B2 | 3/2004 | Gaudiana et al. |
| 6,726,838 B2 | 4/2004 | Shechter et al. |
| 6,827,036 B2 | 12/2004 | Connolly |
| 7,523,370 B1 | 4/2009 | Keller |
| 7,755,675 B2 | 7/2010 | Ejima et al. |
| 2002/0072109 A1 | 6/2002 | Bayless et al. |
| 2002/0146817 A1 | 10/2002 | Cannon et al. |
| 2003/0040104 A1 | 2/2003 | Barbera-Guillen |
| 2003/0056821 A1 | 3/2003 | Chittibabu et al. |
| 2003/0160500 A1 | 8/2003 | Drake et al. |
| 2003/0188777 A1 | 10/2003 | Gaudiana |
| 2003/0189402 A1 | 10/2003 | Gaudiana |
| 2003/0192583 A1 | 10/2003 | Ryan |
| 2003/0192584 A1 | 10/2003 | Beckenbaugh |
| 2003/0192585 A1 | 10/2003 | Beckenbaugh |
| 2003/0230337 A1 | 12/2003 | Gaudiana |

| | | | |
|---|---|---|---|
| 2004/0025933 A1 | 2/2004 | Chittibabu | |
| 2004/0025934 A1 | 2/2004 | Chittibabu | |
| 2004/0031520 A1 | 2/2004 | Ryan | |
| 2004/0089592 A1 | 5/2004 | Shechter et al. | |
| 2004/0118447 A1 | 6/2004 | Muhs | |
| 2004/0118448 A1 | 6/2004 | Scher | |
| 2004/0207102 A1 | 10/2004 | Sugimori et al. | |
| 2004/0209256 A1 | 10/2004 | Dillon | |
| 2004/0262980 A1 | 12/2004 | Watson | |
| 2005/0014239 A1 | 1/2005 | Melis et al. | |
| 2005/0025367 A1 | 2/2005 | Jodoin | |
| 2005/0064577 A1* | 3/2005 | Berzin | 435/266 |
| 2005/0239182 A1* | 10/2005 | Berzin | 435/166 |
| 2005/0260553 A1* | 11/2005 | Berzin | 435/3 |
| 2006/0016760 A1 | 1/2006 | Bozak et al. | |
| 2006/0048920 A1 | 3/2006 | Helleur | |
| 2007/0048848 A1 | 3/2007 | Sears | |
| 2008/0009055 A1 | 1/2008 | Lewnard | |
| 2008/0178739 A1 | 7/2008 | Lewnard | |
| 2009/0011492 A1* | 1/2009 | Berzin | 435/257.1 |
| 2009/0130706 A1 | 5/2009 | Berzin et al. | |

FOREIGN PATENT DOCUMENTS

| | | | |
|---|---|---|---|
| AU | 3000084 A | 1/1985 |
| AU | 543516 B2 | 4/1985 |
| AU | 2294788 A | 4/1989 |
| AU | 654114 B2 | 10/1994 |
| AU | 7131696 A | 4/1997 |
| AU | 704463 B2 | 4/1999 |
| AU | 722744 B2 | 8/2000 |
| AU | 2005274791 A1 | 2/2006 |
| AU | 2007273128 A1 | 1/2008 |
| BR | 9007742 A | 11/1992 |
| CA | 1256770 A1 | 7/1989 |
| CA | 2067348 A1 | 11/1991 |
| CA | 2232707 A1 | 3/1997 |
| DE | 282839 A5 | 9/1990 |
| DE | 3888274 T2 | 9/1994 |
| DE | 4411486 C1 | 3/1995 |
| DE | 4420392 A1 | 12/1995 |
| DE | 69030976 T2 | 10/1997 |
| EP | 0130586 A2 | 1/1985 |
| EP | 0310522 A | 4/1989 |
| EP | 0343885 A1 | 11/1989 |
| EP | 0494887 B1 | 6/1997 |
| EP | 0852616 A1 | 7/1998 |
| EP | 2046938 A2 | 4/2009 |
| EP | 2152848 | 2/2010 |
| ES | 434392 A1 | 4/1977 |
| ES | 2103745 T3 | 10/1997 |
| FR | 2324224 A1 | 4/1977 |
| FR | 2596412 A1 | 3/1986 |
| FR | 2621323 A1 | 4/1989 |
| GB | 1189096 | 4/1970 |
| GB | 1495709 A | 12/1977 |
| GB | 2118572 A | 11/1983 |
| IL | 87832 A | 3/1992 |
| IT | 1033117 B | 7/1979 |
| IT | 01241751 | 10/1990 |
| JP | 50105881 A | 8/1975 |
| JP | 52028990 A | 3/1977 |
| JP | 58035676 B | 8/1983 |
| JP | 1201436 C | 4/1984 |
| JP | 60012913 A | 1/1985 |
| JP | 1108973 A | 4/1989 |
| JP | 02104231 A | 4/1990 |
| JP | 2058896 B | 12/1990 |
| JP | 1630175 C | 12/1991 |
| JP | 5503418 T | 6/1993 |
| JP | 05184347 A | 7/1993 |
| JP | 5184348 A | 7/1993 |
| JP | 05184348 A | 7/1993 |
| JP | 06350119 A | 12/1994 |
| JP | 2645254 B2 | 8/1997 |
| JP | 11075813 A | 3/1999 |
| JP | 2000504924 T | 4/2000 |
| JP | 3061467 B2 | 7/2000 |
| JP | 2001354407 | 12/2001 |
| NO | 921371 A | 6/1992 |
| NO | 981082 A | 5/1998 |
| TW | 519548 B | 2/2003 |
| WO | 9105849 | 5/1991 |
| WO | 9105849 A1 | 5/1991 |
| WO | 9322418 A1 | 11/1993 |
| WO | 9506111 A1 | 3/1995 |
| WO | 9603494 A1 | 2/1996 |
| WO | 9711154 | 3/1997 |
| WO | 9728274 A1 | 8/1997 |
| WO | 9800559 A1 | 1/1998 |
| WO | 9829531 A1 | 7/1998 |
| WO | 0012673 A1 | 3/2000 |
| WO | 0104263 A2 | 1/2001 |
| WO | 0168257 | 9/2001 |
| WO | 0174990 A1 | 10/2001 |
| WO | WO 03015364 | 2/2003 |
| WO | 03038348 A1 | 5/2003 |
| WO | 03067213 A2 | 8/2003 |
| WO | 03094598 | 11/2003 |
| WO | 03094598 A1 | 11/2003 |
| WO | WO03094598 A1 | 11/2003 |
| WO | 2004033075 A1 | 4/2004 |
| WO | 2004074423 A2 | 9/2004 |
| WO | 2005006838 A2 | 1/2005 |
| WO | 2005072254 A2 | 8/2005 |
| WO | 2005079650 A1 | 9/2005 |
| WO | 2005101525 A3 | 10/2005 |
| WO | 2006020177 | 2/2006 |
| WO | 2006020177 A | 2/2006 |
| WO | 2007011343 | 1/2007 |
| WO | 2007038605 | 4/2007 |
| WO | 2008008263 | 1/2008 |
| WO | WO 2008008262 | 1/2008 |
| WO | 2008178739 A1 | 7/2008 |
| WO | 2008134010 A2 | 11/2008 |
| ZA | 7500373 A | 8/1976 |

OTHER PUBLICATIONS

U.S. Appl. No. 11/818,962, John J. Lewnard, Photobioreactor Systems and Methods for Treating CO2-Enriched Gas and Producing Biomass, filed Jul. 10, 2006.

"Biomass Gasification, Research, Development, and Demonstration at the University of Hawaii," pp. 1-4, Aug. 16, 2001, http://www2.ctahr.hawaii.edu/biosystems/Gasifier/index.htm.

"Gas-busters: Algae comes to the aid of coal-fired plants," CNN.com, pp. 1-3, Jul. 31, 2000, http://www8.cnn.com/2000/NATURE/07/31/algae.carbon.enn.

"Gasification and Pyrolysis of biomass," Summary of TAB working report No. 49, pp. 1-4, printed Nov. 26, 2001, from http://www.tab.fzk.de/en/projekt/zusammenfassung/AB49.htm.

"Local Man runner-up in contest at MIT," The Sun Chronicle, Jun. 2, 2002.

"Scientists Look to Cut Greenhouse Emissions," Office of Research Communications, Ohio University, pp. 1-3, Oct. 22, 2001 http://www.ohio.edu/researchnews/Science/co2_plants.htm.

"Scientists Look to Nature to Cut Greenhouse Emissions," Science Daily Magazine, pp. 1-3, Oct. 22, 2001, http://www.sciencedaily.com/releases/2000/07/000720800707.htm.

"Space Life Support From the Cellular Perspective," N.D. Searby, et al., ICES Proceeding 01ICES-331, pp. 1-14 (2001).

"Stimulation of Algae Growth in a Bench-Scale Bubble Column Reactor," Xiaoxi Wu, et al., Biotechnology and Bioengineering, vol. 80, No. 2, 156-158, Oct. 20, 2002.

Antal, Jr., J.J., G. Varhegyi, and E. Jakab (1998) Cellulose Pyrolysis Kinetics: Revisted, Industrial Engineering Chemical Research, vol. 37, pp. 1267-1275.

Antal, Jr., M.J., S.G. Allen, D. Schulman and X. Xu 2000. biomass Gasification in Supercritical Water, Industrial Engineering Chemical Research, vol. 39, pp. 4040-4053.

AU2003234604 Examination Report issued Mar. 27, 2009.

AU2003234604 IDS Submitted Oct. 3, 2007.

Badawy, W.A., "Imrpoved n-Si/oxide junctions for environmentally safe solar energy conversion," Solar Energy Materials and Solar Cells, Elsevier Science Publishers, Amsterdam, NL, vol. 71, No. 3, Feb. 15, 2002, pp. 281-294.

Benemann, John R., and Oswald, William J., "Systems and Economic Analysis of Microalgae Ponds for Conversion of CO2 to Biomass," Final Report to the Department of Energy Pittsburgh Energy Technology Center under Grant No. DE-FG223-93PC93204, Mar. 21, 1996.

Biohydrogen, "Development of Efficient Large-Scale Photogioreactors" James C Ogbonna et al, Chapter 41, "Internal Gas Exchange Photogioreactor" James P Szyper et al, Chapter 53 pp. 329-344 and 441-446, Plenum Press, New York, 1998.

Burlew 1961, et al., "A model integrating fluid dynamics in photosynthesis and photoinhibition processes," Chem. Eng. Sci. 56:3527-3538 2001.

Burlew, John S., Algal Culture, From Laboratory to Pilot Plant, Chapter 9, pp. 105-153; Chapter 11, pp. 166-176; Chapter 17, pp. 235-272; Chapter 18, pp. 273-281, Carnegie Institute of Washington Publication 600, Wahsing, D.C., 1961.

Chao, Kuo-Ping, et al., "Aquacultural characterisets of *Rhizoclonlum riparium* and an evaluation of its biomass growth potential," Journal of Applied Phycology, vol. 17, pp. 67-73, 2005.

Chomet, E., and Czernik S., Renewable Fuels: Harnessing Hydrogen, Nature, vol. 418, pp. 928-929 (2002).

Cortrigh, R. D., R.R. Davda and J.A. Dumesic (2002) "Hydrogen from Catalytic Reforming of Biomass-derived Hydrocarbons in Liquid Water", Nature, vol. 418, 964-967.

Czernik, S., et al., "Hydrogen by Catalytic Steam Reforming of Liquid Byproducts from Biomass Thermoconversion Processes", I&EC Research, vol. 41, pp. 4209-4215 (2002).

Czemik, S., et al., "Hydrogen from Post-Consumer Residues", US DOE Hydrogen, Fuel Cells & Infrastructure Technologies Program—2003 Annual Merit Review Meeting, May 18-22, 2003, Berkeley, CA.

de Luis, J., Vunjak-Novakovic, G., and Searby N.D., Design and Testing of the ISS Cell Culture Unit., Proc. 51st Congress of the Astronautical Federation, rio de Janeiro, Oct. 2-6, 2000.

Dote, Y. et al., "Recovery of liquid fuel from hydrocarbon-rich microalgae by thermochemical liquefaction," Fuel, 1994, 73:12.

Dote, Y., et al., Recovery of liquid fuel from hydrocarbon-rich microalgae by thermochemical liquefaction, Dec. 16, 1993, 3 pages.

Dwi, S., et al., "Utilization of cyanobacterial biomass from water bloom for bioproduction of lactic acid," World Journal of Microbiology & Biotechnology, 17: 259-264, 2001.

Evans, R., et al., "Hydrogen from Biomass: Catalytic Reforming of Pyrolysis Vapors" US DOE Hydrogen, Fuel Cells & Infrastructure Technologies Program—2003 Annual Merit Review Meeting, May 18-22, 2003, Berkeley, CA.

Ginzburg, B., "Liquid Fuel (Oil) From Halophilic Algae: A Renewable Source of Non-Polluting Energy," Renewable Energy, vol. 3, No. 2/3, pp. 249-252, 1993.

Gluz, M.D., et al., Modified Airlift Reactors: The Helical flow Promoters, Chemical Engineering Science, vol. 51, No. 11, pp. 2915-2920, 1996.

Gratzel, M., Molecular Photovoltaics and Mimic Photosynthesis, Pur Appl. Chem, 73:459 (2001).

Gratzel, M., Photoelectrochemical Cells, Nature, 414:338 (2001).

Gray, "Fundamentals of Bitumen Coking Processes Analogous to Granulations: A Critical Review", The Canadian Journal of Chemical Engineering, vol. 80, pp. 393-401, Jun. 2002.

Gupta, P., "Monte Carlo Stimulation of NaI Detectors Efficiencies for Radioactive Particle Tracking in Multiphase Flows", CREL, Annual Report, Washington University, p. 117 (1998).

Hamasaki, M., et al., "Influence of CO2, SO2 and NO in flue gas on microalgae productivity," Journal of Chemical Engineering of Japa, 30 (4): 620-624, Aug. 1997, Abstract.

Handbook of Microalgal Culture, Edited by Amost Richmond, "Mass Production of Microalgae: Photobioreactors," Mario R. Tredici, Chapter 9, Blackwell Science, Ltd., Oxford, United Kingdom, 2004, pp. 178-214.

Ike, A., et al., "Algal CO2 fixation and H2 Photoproduction," In BioHydrogen, Zaborsky et al., eds. Plenum Press, New York, pp. 265-271 (1998).

Ike, A., et al., "Hydrogen Photoproduction from CO2-Fixing Microalgal Biomass: Application of Lactic Acid Fermentation by *Lactobacillus amylovorus*," Journal of Fermentation and Bioengineering, vol. 84, pp. 428-433 (1997).

Ikuata, Y., et al., "Hydrogen Production by Photosynthetic Microorganisms," In bioHydrogen, Zaborsky et al., eds. Plenum Press, New York, pp. 319-327 (1998).

Intenrational Preliminary Report on Patentability dated Oct. 26, 2006 (PCT/US2005/013108).

International Application No. PCT/US2007/015513 Written Opinion issued Jan. 10, 2009.

International Application PCT/2003/15364 Response to Written Opinion Jun. 1, 2004.

International Application PCT/US2003/15364 Response to Written Opinion.

International Application PCT/US2005/025249 IPRP issued Jan. 18, 2008.

International Application PCT/US2005/025367 IPRP issued Jan. 16, 2007.

International Application PCT/US2007/015513 IPRP issued Jan. 13, 2009.

International Patent Application PCT/US2006/37685 Search Report and Written Opinion issued Apr. 2, 2007.

International Preliminary Examination Report PCT/US03/15364 issued Aug. 10, 2004.

International Preliminary Examination Report, PCT/US03/15364, issued Aug. 10, 2004.

International Preliminary Examination Report, PCT/US08/005383, dated Nov. 5, 2009.

International Preliminary Report on Patentability from International Patent Application No. PCT/US2005025249, dated Jan. 31, 2008.

International Preliminary Report on Patentability, (PCT/US2005/025367) Issued Jan. 25, 2007.

International Preliminary Report on Patentability, PCT/US2008/005383, issued Oct. 27, 2009.

International Search Report (PCT/2003/15364) issued Sep. 3, 2003.

International Search Report and Written Opinion (PCT/US2005/25367) issued Jan. 5, 2006.

International Search Report and Written Opinion from International Patent Application No. PCT/US2007/015514, dated Nov. 23, 2007.

International Search Report and Written Opinion PCT/US2005/013108 issued Jan. 12, 2006.

International Search Report and Written Opinion PCT/US2007/015513, issued Feb. 28, 2008.

International Search Report and Written Opinion, dated Jan. 1, 2006 (PCT/US2005/013108).

International Search Report and Written Opinion, PCT/US2009/040818, issued Jul. 13, 2009.

International Search Report andWritten Opinion from International Patent Application No. PCT/US2007/015513, dated Feb. 2, 2008.

International Search Report PCT/US03/15364 issued Sep. 3, 2002.

John R. Benemann, et al. "Systems and Economic Analysis of Microalgae Ponds for Conversion of CO2 to Biomass" Final Report to DOE Pittsburgh Energy Tech Center, 1996.

Kumar, B.S., et al., A y-ray Tomographic Scanner for Imaging of Void Distribution in Two-Phase Flow Systems, Flow Meas. Instrum., 6(3), 61 (1995).

Kumar, et al., Gas Holdup Measurements in Bubble Columns Using Computed Tomography, AIChE J., 43(6), 1414 (1997).

LaMonica, Martin, "Start-up drills for oil in algae," CNET Press Release, pp. 1-4, May 20, 2005, http://www.news.com.

Larachi, et al., A gamma-ray Detection System for 3D Particle Tracking in Multiphase Reactors, Nucl. Instr. & Meth., A338, 568 (1994).

Laskin, I. and Lechevalier, H.A., Editors, CRC Handbook of Microbiology, Cleveland CRC Press, pp. 519-552 (1977).

Lee, Yuan-Kun, "Enclosed bioreactors for the mass cultivation of photosynthetic microorganisms: the future trend," TIBTECH, Jul. 1986, Elsevier Science Publishers B.V., Amsterdam, pp. 186-189.

Liberman, "Studies of the Chemistry of Hydrocarbons and Their Catalytic Conversions", vol. 30, No. 5, pp. 237-251, (1961).

Magrini-Bair, K. et al., Fluidizable Catalysts for Hydrogen Production from Biomass Pyrolysis/Steam Reforming, US DOE Hydrogen, Fuel Cells & Infrastructure Technologies Program—2003 Annual Merit Review Meeting, May 18-22, 2003, Berkeley, CA.

Maness and Weaver "Hydrogen Production From a Carbon-Monoxide Oxidation Pathway in Rubrivivax gelatinosus", International J. Hydrogen Energy, vol. 27, pp. 1407-1411 (2002).

Marra, J. "Phytoplankton Phosynthetic Response to Vertical Movement in a Mixed Layer", Mar. Biol. 46:203, 1978.

Merchuk, et al., "Comparison of photobioreactors for cultivation of the red microalga *Porphyridium* sp," J Chem Technol Biotechnol, 75:1119-1126 (2000).

Merchuk, J., "Why use air-lift bioreactors?", Tibtech, Mar. 1990, vol. 8, pp. 66-71.

Merchuk, J.C., et al., "Light/Dark Cycles in the Growth of the Red Microalga *Porphyridium* Sp.," Biotechnology and Bioengineering, vol. 59, No. 6, Sep. 20, 1998, pp. 705-713.

Mercury Study Report to Congress, EPA-452/R-97-010, vol. VIII (1997).

Mercury Study Report to congress, EPA-452/R-97-010, vol. VIII, (1997).

Miura, Y. et al., "Stimulation of Hydrogen Production in algal Cells Grown Under High CO2 concentration and Low Temperature," Applciced Biochemistry and Biotechnology, vol. 39/40, pp. 753-761 (1993).

Morita, et al., "Instruciton of microalgal biomass production for practically high photosynthetic perormance using a photobioreactor," Food and Bioproducts Processing, 79 (C3): 176-183 Sep. 2001.

Morita, M., Y. Watanabe and H. Saiki, "Instruction of Microalgal Biomass Production for Practically Higher Photosynthetic Performance Using a Photobioreactor," Trans IchemE., vol. 79, Part C, Sep. 2001.

Nagase, et al., "Improvementof Microalgal NOx Rremoval in Bubble Column and Airlift Reactors," Journal of Fermentation and Bioengineering, vol. 86, No. 4, pp. 421-423, 1998.

Nagase, Hiroyasu, et al., "Characteristics of Biological NOx Removal from Flue Gas in a *Dunaliella tertiolecta* Culture System," Journal of Fermentation and Bioengineering, 83, 1997.

Office Action for Eurasian Application No. 200401492 based on PCT Appl. No. US03/15364 (and claims as pending as of Jun. 2006).

Ogbanna, James C., et al., BioHydrogen, "Development of Efficient Large-Scale Photobioreactors," Chapter 41, "Internal Gas Exchange Photobioreactor," James P. Szyper, et al., Chapter 53, pp. 329-344 and 441-446, Plenum Press, New York, 1998.

O'Regan B., et al., A Low Cost High Efficiency Solar Cell Based on Dye-Sensitized Colloidal TiO2 Films, Nature, 353:737, (1991).

Osburn, L., "Hemp for Fuel" Schaffer Library of Drug Policy, pp. 1-3, printed Nov. 26, 2001, from http://www.druglibrary.org/schaffer/hemp/hempfuel.htm.

Oswald, William J., "The Engineering Aspect of Microalgae," CRC Handbook of Microbiology, Edited by I. Laskin and H.A. Lechevalier, Cleveland CRC Press, 1977, pp. 519-552.

Otsuki, Toshi, et al., "Hydrogen Production by a Floating-Type Photobioreactor," BioHydrogen, Chapter 45, Plenum Press, New York, 1998, pp. 369-374.

PCT/US08/005383 Publication with Search Report.

Pulz, O., "Photobioreactors: production systems for photorophic microorganisms," Appl Microbiol Biotechnol 57:287-293, Aug. 22, 2001.

Pulz, Otto, et al., "Photobioreactors: Design and Performance with Respect to Light Energy Input," Advances in Biochemical Engineering/Biotechnology, pp. 124-152, vol. 59, 1998.

Rake, M., "A burning issue," Perspectives, Spring and Summer 1999, pp. 1-7.

Reed, T. B., and Gaur S. "A Survey of Biomass Gasification" NREL, 2001.

Richmond, Amos, Handbook of Microalgal Culture, Biotechnology and Applied Phycology, Chapter 8 and Ian S.F. Jones, Chapter 33, pp. 125-177 and 534-544, Blackwell Science Ltd., Oxford, United Kingdom, 2004.

Roessler, P. G., et al., "Genetic Engineering Approaches for Enhanced Proudction of Biodiesel Fuel from Microalgae," National Renewable Energy Laboratory, Golden, CO, 1993.

Rogers, L.J. and Gallon J.R. "Biochemistry of the Algae and Cyanobacteria," Clarendon Press Oxford, 1988.

Round, F. E., The Biology of the Algae, St. Martin's Press, New York, 1965.

Scherzer, et al., Hydrocracking Science and Technology, Marcel Dekker, Inc. (1996).

Schlotelburg, C., et al., "Characterization of an Airlift Reactor with Helical Flow Promoters," The Canadian Journal of Chemical Engineering, vol. 77, Oct. 1999, pp. 804-810.

Searby, N. D., et al., "Space Life Support from the Cellular Perspective," ICES Proceeding 011CES-331, pp. 1-14 (2001).

Searby, N.D., de Luis, J. and Vunjak-Novakovic, G., Design and Development of a Space Station Cell Culture Unit., J. Aerospace, vol. 107, pp. 445-457 (1998).

Sheehan, John, Dunhay Terri, Benemann, John R., Roessler Paul, "A Look Back at the U.S. Department of Energy's Aquatic Species Program: Biodiesel from Algae," 1998, NERL/TP-580-24190.

Shimamatsu, H., "Mass production of *Spirulina*, an edible microalga," Hydrobiologia, 512: pp. 39-44, 2004.

Soule, A., "Greenfuel mixes algae, carbon dioxide to create oil," Mass High Tech, The Journal of New England Technology, Dec. 5, 2001, pp. 1-3.

Sterling, B, "Hiding the Garbage," Viridian Note 00270: pp. 1-6.

Sung S., et al., "Biohydrogen Production from Renewable Organic Wastes", US DOE Hydrogen, Fuel Cells & Infrastructure Technologies Program—2003 Annual Merit Review Meeting, May 18-22, 2003, Berkeley CA.

The Algae Alternative, Evan I. Schwartz, The Bostom Globe, Jul. 12, 2004.

Tredici, Mario R., Handbook of Microalgal Culture, Edited by Amos Richmond, Mass Production of Microalgae: Photobioreactors, Chapter 9, Blackwell Science Ltd., Oxford, United Kingdom, 2004, pp. 178-214.

Trinity-Stevens, A., "Scientist Searches Yellowstone Park for Carbon Dioxide-Eating Microbe," Montana State University Communications Services, pp. 1-2.

Ugwu, C. U., et al., "Design of static mixers for inclined tubular photobioreactors," Journal of Applied Phycology, vol. 15, pp. 217-223, 2003.

Ugwu, C. U., et al., "Improvement of mass transfer characteristics and productivities of inclined tubular photobioreactors by installationof internal static mixers," Appl Microbiol biotechnol (2002) 58:600-607.

U.S. Appl. No. 10/514,224 NonFinal Office Action Jun. 11, 2009.

U.S. Appl. No. 11/818,962 Non-Final Office Action issued Jun. 11, 2010.

U.S. Appl. No. 11/818,962 Non-Final Office Action Response filed Nov. 11, 2010.

U.S. Appl. No. 12/110,178 Non-Final Office Action issued Sep. 29, 2010.

U.S. Appl. No. 12/110,178 Preliminary Amendment filed Dec. 29, 2008.

U.S. Appl. No. 10/514,224 Information Disclosure Statement filed Mar. 19, 2007.

U.S. Appl. No. 11/514,224 Non-Final Office Action issued Jun. 11, 2009.

Van Ginkel, S., et al., "Biohydrogen Production as a Function of pH and Substrate Concentration", Environmental Science & Technology, vol. 35, pp. 4726-4730 (2001).

Vunjak-Novakovic, Gordana, et al., "Air-Lift Bioreactors for Algal Growth on Flue Gas: Mathematical Modeling and Pilot-Plant Studies," Ind. Eng. Chem. Res. 2005, vol. 44, pp. 6154-6163.

Vunjak-Novakovic, Gordana, et al., "Microgravity Studies of Cells and Tissues," Ann. N. Y. Acad. Sci. 974:504-517 (2002).

Watanabe, et al., "Photosynthetic CO2 conversion technologies using a photobioreactor incorporation microalgae-Energy and material balances," Energy Conversion and Management, 37 (6-8): 1321-1326 Jun.-Aug. 1996, Abstract.

Wolfrum, E., et al., "Biological Water Gas Shift", US DOE Hydrogen, Fuel Cells & Infrastructure Technologies Program—2003 Annual Merit Review Meeting, 18-22, 2003, Berkeley, CA.

Written Opinion, PCT/US08/005383, dated Apr. 9, 2009.

Wu, Xiaoxi and Merchuk, Jose, C., "A model Integrating fluid dynamics in photosynthesis and photoinhibition processes," Chemical Engineering Science, 2001, 56, pp. 3527-3538.

Wu, Xiaoxi, et al., "Stimulation of Algae Growth in a Bench-Scale Bubble column Reactor," Biotechnology and Bioengineering, vol. 80, No. 2, 156-168, Oct. 20, 2002.

Xiaoxi Wu, et al., Measurement of fluid flow in the downcomer of an internal loop airlift reactor using an optical trajectory-tracking system, Chemical Engineering Science 58 (2003) 1599-1614.

Xiaoxi, Wu, et al., "Simulation of Algae growth in a bench scale internal loop airlift reactor," Chemical Engineering Science 59 (2004) 2899-2912.

Yuan-Kun Lee, "Enclosed Bioreactors for the mass cultivation of photosynthetic microorganisms: the future trend," TIBTECH, Jul. 1986, Elsevier Science Publishers B.V., Amsterdam, pp. 186-189.

Zimmerman, J., "Algae emissions reduction concept shows new promise,", Electric Light & Power/Utility Automation and Engineering T&D News, printed Apr. 19, 2005, pp. 1-3.

* cited by examiner

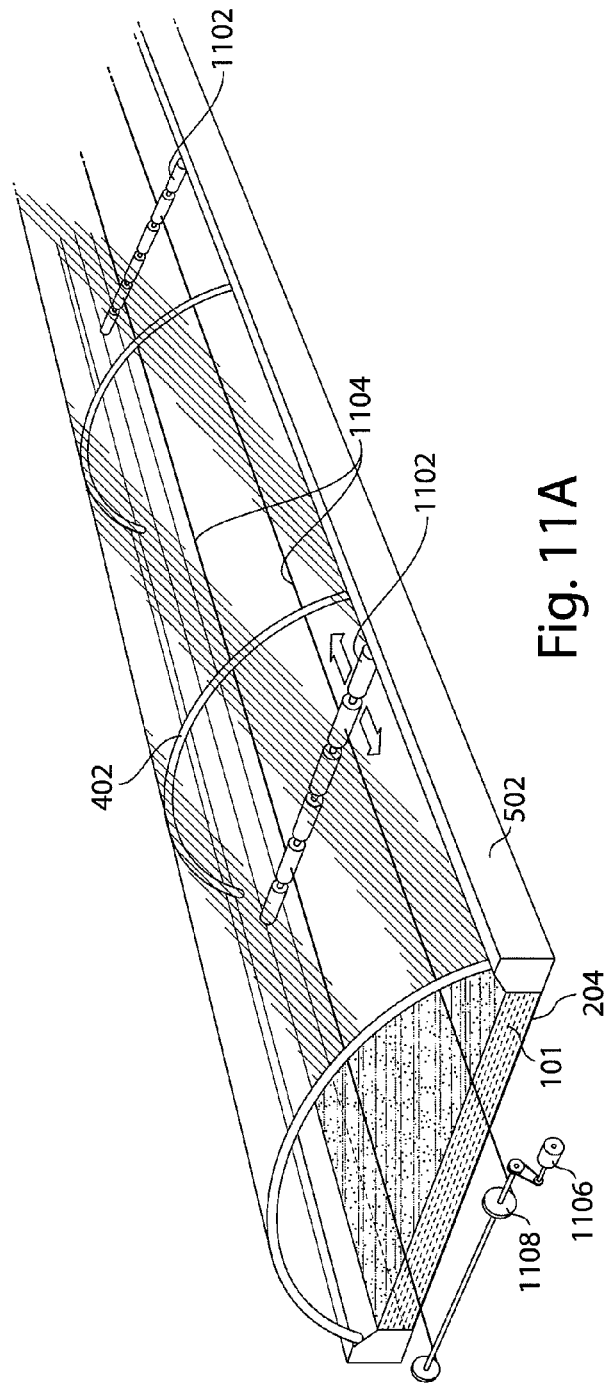
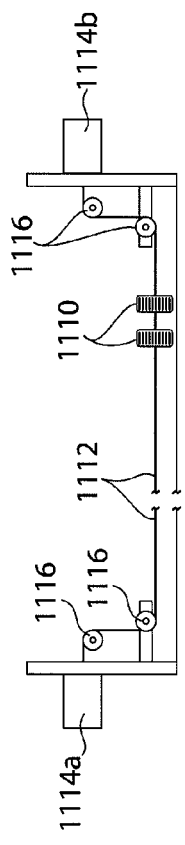
Fig. 11A
Fig. 11B

PHOTOBIOREACTOR SYSTEMS POSITIONED ON BODIES OF WATER

RELATED APPLICATIONS

This application claims priority under 35 U.S.C. §119(e) to U.S. Provisional Application Ser. Nos. 60/926,622 and 60/926,569, each entitled "Photobioreactor Systems Positioned on Bodies of Water," and filed on Apr. 27, 2007, each of which is herein incorporated by reference in its entirety.

FIELD OF THE INVENTION

The invention relates generally to photobioreactors, particularly floating photobioreactors, and processes to operate and use the photobioreactors for the production of biomass, and for the treatment of gases, such as flue gases and/or carbon dioxide-enriched gases.

DISCUSSION OF THE RELATED ART

The global market for fossil feedstocks for transportation fuels is increasingly characterized by tight supplies and threats resulting from geopolitical instability leading to increasing calls for clean, reliable, domestic sources of liquid fuel. Production of ethanol derived from corn is rapidly increasing to meet this demand, urged on by government incentives, but the net energy gain of corn ethanol is modest at best, and the feedstock is subject to competitive demand from food and feed markets. Conversion of soybean oil to biodiesel is also increasing, but production capacity is likewise constrained by competing demand. Cellulosic ethanol derived from switchgrass and crop residues is an area of active research, but the process is not economical at present, and significant progress is needed to make it competitive. As the market for biofuels grows, feedstock production increasingly competes with food and livestock interests for a limited amount of good agricultural land and clean irrigation water, and so a need is developing for biofuel feedstocks that do not require or require less of these resources.

Evidence is increasing that significant global warming is occurring as a result of human activities, chiefly the release of massive quantities of carbon dioxide from the burning of coal, oil, and other fossil fuels. These fuels are used not only for transportation, but also for electricity generation, industrial processes, and heating. Concerns relating to potential political, economic, and agricultural disruptions resulting from climate change have led to modest initial efforts to reduce global carbon dioxide emissions, such as the Kyoto Protocol. The prospect of further carbon dioxide control measures such as possible emission caps and carbon taxes have also spurred interest in renewable, "carbon-neutral" biofuels.

Because the burning of fossil fuels provides the majority of the energy used by humans, a reduction in fossil fuel use could have a significant economic impact unless alternative energy sources were available to offset the reductions. Another possibility is separation of carbon dioxide from fossil fuel exhaust gas streams, followed by sequestration or recycling.

One approach that addresses the problem of carbon dioxide emissions is the use of flue gas as a carbon source to accelerate the growth of photosynthetic algae. Algae are the fastest growing plants on earth and one of nature's simplest microorganisms, and they are also one of the most efficient converters of carbon dioxide and solar energy to biomass. Certain previous efforts at using algae for fuel production or carbon dioxide mitigation have employed different approaches but because of various problems, addressed by certain embodiments of the present invention, they have encountered various difficulties that have limited their technical and commercial success.

SUMMARY

Certain embodiments and aspects of the present invention relate to photobioreactor apparatus and biomass production and/or gas treatment systems and methods employing photobioreactors. The methods and apparatus are used for carbon dioxide bio-regeneration, pollutant mitigation, and/or biomass production.

According to one aspect of the invention, a photobioreactor is provided in which a gas containing elevated concentrations of carbon dioxide is contacted with a liquid medium containing a phototrophic biological species such as algae. The gas and liquid are contained within an elongated photobioreactor unit having a light-transparent cover, and the biological species uses the carbon dioxide and the light to grow, thereby producing biomass. The elongated photobioreactor unit may be floated on a water body such as a pond, lake, or ocean, and various structures and methods for mixing the liquid medium and/or maintaining a constant thickness of the liquid medium may be used. One or more of the photobioreactor units operating in parallel may form a photobioreactor system. However, some embodiments of photobioreactor systems may include a single photobioreactor unit (formed of multiple photobioreactor sections) or even a single photobioreactor section. In some embodiments, systems may include one or more substantially circular photobioreactor units, and/or photobioreactors having other shapes.

According to another aspect of the invention, a bioreactor is formed of a transparent flexible plastic sealed enclosure floating on the surface of a pond or other body of water. The sealed enclosure contains a closed volume of aqueous algal culture below and a volume of carbon dioxide-rich gas above. When the enclosure is exposed to sunlight, the photosynthetic algal organisms convert carbon dioxide from the gas above, thereby producing valuable biomass and recapturing carbon dioxide that would otherwise be released to the atmosphere. Temperature swings in the algal culture are mitigated by thermal communication with the large thermal mass of the pond, for example through a thin barrier biologically separating the algal culture from the pond. The enclosure may be agitated mechanically to prevent stagnation, increase the rate of carbon dioxide uptake, improve heat transfer, introduce light distribution, and/or distribute nutrients. When the algal culture has reached a selected density and/or carbon dioxide conversion has progressed to a selected end point, the biomass may be harvested, e.g. by opening the enclosure.

According to another aspect of the invention, a liquid medium containing photosynthetic organisms therein may be continuously flowed through an enclosed photobioreactor, and carbon dioxide-enriched gas also may be continuously flowed through the photobioreactor—either in the same direction or in a direction opposite to the liquid medium flow.

According to another aspect of the invention, a flexible, rigid or semi-rigid structure is used to stabilize the shape of the photobioreactor, maintain the photobioreactor's orientation, and/or maintain the liquid medium at a substantially constant depth within the enclosure.

In some embodiments, an upper transparent barrier film and a lower barrier film are connected to two parallel floating edge supports to enclose a volume. A layer of aqueous algal culture is provided at the bottom of the volume, and a gas headspace is formed above the algal culture. A plurality of transverse members apply an outward force on the edge supports, and this force tensions the lower barrier film such that the lower barrier film is held substantially flat. With a substantially flat lower barrier film, the algal culture may be maintained at a substantially constant thickness.

According to another aspect of the invention, mixing is provided within the algal culture. In some embodiments, solid elements are moved through the liquid medium to mix the contents therein. In other embodiments, wave propagation and/or transverse and/or longitudinal oscillation of the photobioreactor are used. In still other embodiments, bulk circulation of the liquid medium is employed.

According to another aspect of the invention, a plurality of floating enclosures are automatically handled by a conveyance system configured to move the floating enclosures around a water body. In some embodiments, a cable drive system is used to transport the floating enclosures.

According to one aspect of the invention, an enclosed photobioreactor is configured to float on a body of water, and the photobioreactor includes an elongated, longitudinally-oriented photobioreactor section constructed and arranged to contain a liquid medium comprising phototrophic organisms therein. The photobioreactor section includes a substantially flexible lower barrier comprising an upper surface in contact with and supporting the liquid medium, and a cover constructed and arranged to cover the liquid medium within the photobioreactor section and further constructed and arranged to provide a gas headspace under the cover and above the liquid medium, the cover being at least partially transparent to light of a wavelength capable of driving photosynthesis. The photobioreactor section further includes a first floatation element disposed on a first lateral side of the photobioreactor section, and a second floatation element disposed on a second lateral side of the photobioreactor section. The first and second floatation elements are constructed and arranged to support the photobioreactor section for floatation on the body of water. The photobioreactor further includes a plurality of tensioners constructed and arranged to apply tension to the lower barrier so as to maintain a substantial portion of the area of the lower barrier in a substantially horizontal configuration when the photobioreactor section is charged with the liquid medium, such that a continuous layer of the liquid medium has a substantially uniform depth which extends from approximately the first floatation element to approximately the second floatation element over at least a portion of the area of the lower barrier.

According to another embodiment, an enclosed photobioreactor is configured to float on a body of water and the photobioreactor includes an elongated, longitudinally-oriented photobioreactor section constructed and arranged to contain a liquid medium comprising phototrophic organisms therein. The photobioreactor section includes a substantially flexible lower barrier comprising an upper surface in contact with and supporting the liquid medium, and a cover constructed and arranged to cover the liquid medium within the photobioreactor section and further constructed and arranged to provide a gas headspace under the cover and above the liquid medium, the cover being at least partially transparent to light of a wavelength capable of driving photosynthesis, and the gas headspace being fluidically connected to a source of carbon dioxide-enriched gas. In addition, the photobioreactor section includes a first floatation element disposed on a first lateral side of the photobioreactor section, and a second floatation element disposed on a second lateral side of the photobioreactor section. The first and second floatation elements are constructed and arranged to support the photobioreactor section for floatation on the body of water. A plurality of floats are positioned between the first and second floatation elements, the floats being constructed and arranged to float in the liquid medium and support the lower barrier so as to maintain a substantial area of the lower barrier in a substantially horizontal configuration when the photobioreactor section is charged with the liquid medium, such that a continuous layer of the liquid medium has a substantially uniform depth which extends from approximately the first floatation element to the second floatation element over at least a portion of the area of the lower barrier.

According to a further embodiment, an enclosed photobioreactor is configured to float on a water body, and the photobioreactor includes a photobioreactor section constructed and arranged to contain a liquid medium comprising phototrophic organisms therein. The photobioreactor section includes a lower barrier comprising an upper surface in contact with and supporting the liquid medium, and a cover constructed and arranged to cover the liquid medium within the photobioreactor section and further constructed and arranged to provide a gas headspace under the cover and above the liquid medium, the cover being at least partially transparent to light of a wavelength capable of driving photosynthesis. A mechanical mixing system includes at least one mixing element, and the mixing system is constructed and arranged to move the mixing element such that the mixing element contacts and mixes the liquid medium.

According to another embodiment, a method of producing biomass includes floating an enclosed photobioreactor on a body of water, the photobioreactor being configured to permit the transfer of heat between liquid medium contained in the photobioreactor and the body of water. The method further includes transferring waste heat produced by an industrial process to the body of water, thereby heating the water in the body of water and the liquid medium contained in the photobioreactor.

According to a further embodiment, a photobioreactor system includes a plurality of separate, sealed photobioreactor units floating on a body of water, and each photobioreactor unit contains a liquid medium comprising at least one species of phototrophic organisms therein. The system also includes a conveyor system configured to move the plurality of sealed photobioreactors around the body of water.

According to another embodiment, a method of generating biomass includes providing a plurality of photobioreactor units constructed primarily of substantially flexible material. The method further includes introducing liquid medium comprising phototrophic organisms therein into each of the photobioreactor units, sealing the photobioreactor units, and floating the photobioreactor units on a body of water.

According to a further embodiment of the invention, a method of growing macroalgae in a photobioreactor system includes floating, on a body of water, a longitudinally oriented enclosed photobioreactor section constructed primarily of a substantially flexible material and having a cross-sectional shape, for a cross-section taken essentially perpendicular to a longitudinal axis of the photobioreactor section, that is characterized by at least a portion of its perimeter being curved, when in operation. The method further includes introducing a liquid medium comprising macroalgae therein into the photobioreactor section, introducing a carbon dioxide-enriched gas into the photobioreactor section to form a gas headspace, and moving and reorienting the macroalgae within the liquid medium by mixing the liquid medium.

BRIEF DESCRIPTION OF THE DRAWINGS

Other advantages, novel features, and uses of the invention will become more apparent from the following detailed description of non-limiting embodiments of the invention when considered in conjunction with the accompanying drawings, which are schematic and which are not intended to be drawn to scale. In the figures, each identical, or substantially similar component that is illustrated in various figures is typically represented by a single numeral or notation. For purposes of clarity, not every component is labeled in every figure, nor is every component of each embodiment of the invention shown where illustration is not necessary to allow those of ordinary skill in the art to understand the invention.

In the drawings:

FIG. 2b is a cross-sectional view of the longitudinal photobioreactor section illustrated in FIG. 2a.

FIG. 4a is a front view of a longitudinal photobioreactor section having tensioners according to another embodiment of the invention;

FIG. 4b is a perspective view of the embodiment illustrated in FIG. 4a;

FIG. 4c is a side view of a photobioreactor section having selectively deployable dividers;

FIG. 11a is a perspective view of a photobioreactor including a mixing system, according to one embodiment of the invention;

FIG. 11b is a schematic side view of a photobioreactor including a mixing system, according to one embodiment of the invention;

DETAILED DESCRIPTION

Figure 1:
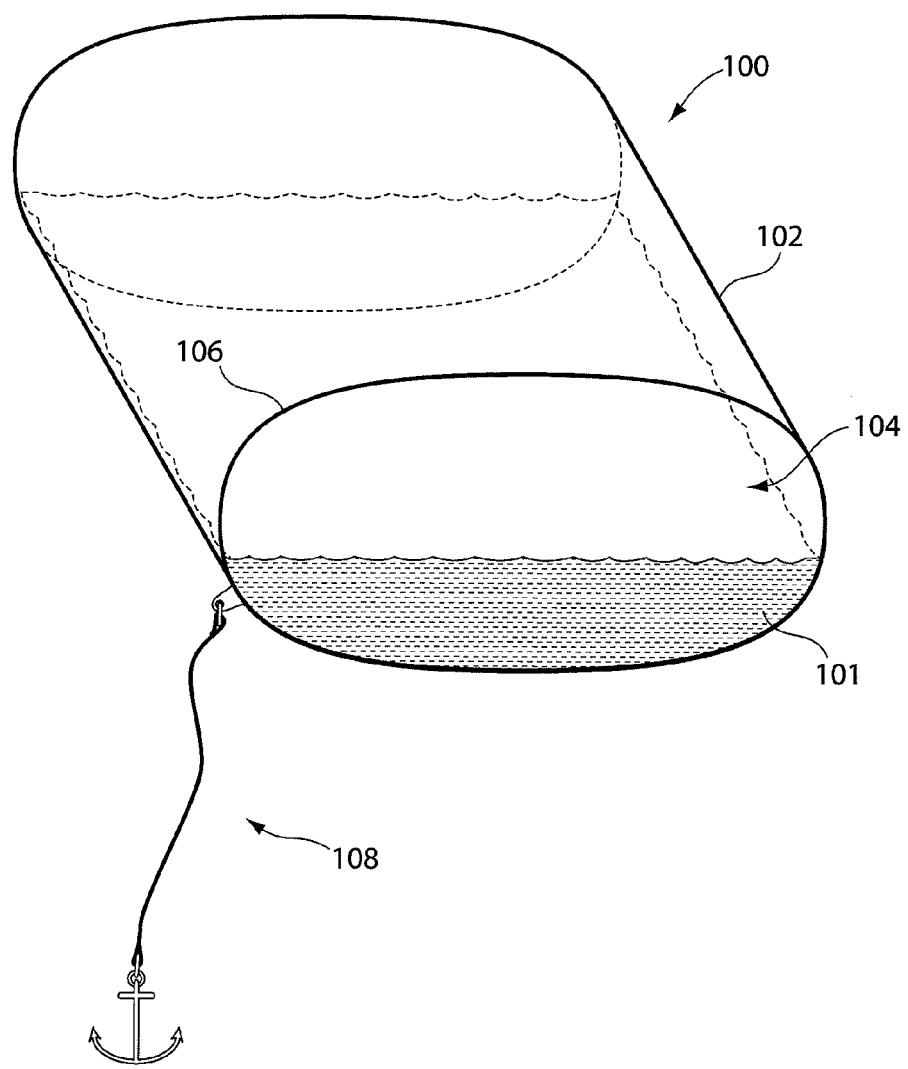
FIG. 1 is a perspective view of a floatable photobioreactor section according to one embodiment of the invention.

Certain embodiments and aspects of the present invention relate to photobioreactor systems designed to contain a liquid medium comprising at least one species of phototrophic organism therein and to methods of using the photobioreactor systems to produce biomass and/or as part of a gas-treatment process and system able to at least partially remove certain components from a gas stream.

Certain embodiments of the invention include one or more elongated, longitudinally oriented (equivalently "longitudinal" as used herein), photobioreactor units having a flexible lower barrier and configured to float on a body of water to form at least a part of a photobioreactor system. In certain embodiments, each photobioreactor unit has a liquid channel and a gas headspace enclosed by a light-transparent cover. A gas feed, such as a carbon dioxide-enriched gas enters the photobioreactor unit and flows in the headspace above a liquid medium comprising at least one phototrophic organism such as algae. The algae uses the carbon dioxide from the gas and the light that passes through the cover to grow and produce biomass. Algae may be harvested from the liquid medium discharge and dewatered. The dewatered algae may go through additional processes and may be used as fuel and/or used to produce a fuel product (e.g. biodiesel). In some cases, the photobioreactor units may be on the order of a few hundred feet in length or less, while in other cases, the photobioreactor units may extend half a mile or more. In certain embodiments, a photobioreactor unit is in the form of a single photobioreactor section having a length equal to the total length of the photobioreactor unit. In other embodiments, a photobioreactor unit may be comprised of multiple photobioreactor sections interconnected in series. In certain embodiments, an overall photobioreactor/photobioreactor system may comprise multiple photobioreactor units connected in parallel.

Many power plants and other industrial facilities include ponds or other bodies of water to which, in certain cases, waste heat is discharged. In some embodiments, especially in colder climates, a photobioreactor may be positioned on top of a pond to which waste heat is discharged to achieve one or more possible advantages. By floating or otherwise positioning a bioreactor on a body of water, the photobioreactor system may take advantage of the inherent flatness of the surface of a body of water over an expansive area. Further, by using an already existing pond, limited additional geographic land area is required to accommodate the photobioreactor system. The pond can also act as a heat source or heat sink to modulate the temperature of the liquid medium in the photobioreactor. For example, if the body of water accepts heated wastewater from the power plant (or other source) the photobioreactor system can be heated by the body of water to improve biomass production and/or prevent freezing in cold ambient conditions.

Certain embodiments of the invention include sealed photobioreactor units which are not necessarily elongated in orientation and which are used in batch mode or semi-batch mode. Such units may be constructed with thin, flexible materials, such as plastic, and floated on a body of water once charged with liquid medium and gas.

In certain embodiments, the disclosed photobioreactor systems, methods of using such systems, and/or gas treatment systems and methods provided herein can be used as part of an integrated method and system for treating flue, exhaust, or waste gasses produced by industrial processes, wherein phototrophic organisms used within the photobioreactor at least partially remove certain pollutant compounds contained within effluent gases, e.g. $CO_2$ and/or $NO_x$, and are subsequently harvested from the photobioreactor system, processed, and used as a fuel source or converted to a fuel source for a combustion device (e.g. an electric power plant generator, industrial furnace and/or incinerator, automobile, etc.). Such uses of certain embodiments of the invention can provide an efficient means for recycling carbon contained within a combustion fuel (i.e. by converting $CO_2$ in a combustion gas to biomass fuel, biomass-derived fuel, biomass feed, and/or nutraceuticals in a photobioreactor system), thereby reducing both $CO_2$ emissions and fossil fuel requirements.

Because even the most productive algae strains convert at best a few percent of incident solar radiation to chemical energy, substantial amounts of heat may be delivered to the liquid medium when the sun is shining, and periodic or continuous removal of heat from the liquid medium may be desirable. In some circumstances, particularly in colder climates, periodic or continuous heating of the liquid medium is desirable.

By floating enclosed photobioreactors on a body of water, provision may be made for passive thermal control of culture (i.e., liquid medium) temperature while maintaining biological isolation of the liquid medium from the body of water via the enclosed nature of the photobioreactor. Many photobioreactors benefit from active thermal control to maintain the algal culture at acceptable growth temperatures, and the active thermal control may involve extensive energy input/output. Thermal control (whether active or passive) may be beneficial when the liquid medium is provided at a thickness in which the liquid medium itself does not provide an adequate heat sink.

It has been determined within the context of the present invention that the culture temperature (i.e., liquid medium temperature) may be maintained within a desirable range of difference with respect to the temperature of a supporting body of water on which certain photobioreactors of the present invention float by modest mixing of the liquid medium when the thickness of the barrier between the liquid medium and the supporting body of water is less than about 5 mm and is constructed from appropriate materials, as discussed below. In some embodiments, a barrier having a thickness of no more than 3 mm is used, and in some embodiments a barrier having a thickness of no more than 100 microns is used. For example, the culture temperature (i.e., liquid medium temperature) may be maintained within about 5 degrees F. of the temperature of a supporting body of water on which certain photobioreactors of the present invention float by modest mixing of the liquid medium when the thickness of the barrier between the liquid medium and the supporting body of water is less than approximately 1 mm and is constructed from appropriate materials. Further, manipulation of the water body temperature may be accomplished, whether by controlled addition of warm or cool waste water flows, or by controlling the degree of evaporation and thermal stratification in the pond. In dry environments, heat loss from a pond or lake is dominated by evaporative cooling; this cooling may be reduced by blanketing the surface with floating materials, or augmented by means of aerators or fountains, if desired to maintain a desirable temperature range. Also, when heat is delivered to the surface of a body of water, thermal stratification tends to prevent vertical mixing, such that the upper layer of the body can remain significantly warmer than the lower layer. This stratification occurs naturally in a pond covered with floating photobioreactors, and it may be used to increase the operating temperature of the photobioreactors of the invention. Alternatively, the pond (or other body of water) can be mechanically mixed, and in particular, vertically mixed, to homogenize the body of water and reduce the surface temperature if it is desirable to reduce the liquid medium temperature.

Certain embodiments may be implemented on a water body that experiences tidal variations. In this manner, the water body may cool the photobioreactor, and the heated water may be replaced during a tide change with unheated water.

The photobioreactor sections may be heated or cooled and maintained at certain temperatures or temperature ranges suitable or optimal for productivity. These specific, desirable temperature ranges for operation will, of course, depend upon the characteristics of the phototrophic species used within the photobioreactor systems, the type of photobioreactor, the ambient temperature, the intensity or solar irradiation, etc. Typically, it is desirable to maintain the temperature of the liquid medium between about degrees C. and about 45 degrees C., more typically between about 15 degrees C. and about 37 degrees C., and most typically between about 15 degrees C. and about 25 degrees C. For example, a desirable temperature operating condition for a photobioreactor utilizing *Chlorella* algae could have a liquid medium temperature controlled at about 30 degrees C. during the daytime and about 20 degrees C. during nighttime. In one embodiment, the temperature of the photobioreactor is maintained at about 20 degrees C.

According to another aspect of the invention, certain inventive photobioreactors are constructed of flexible and deformable materials, e.g. thin plastic sheeting, and various structures are used to stabilize the shape of a flexible photobioreactor, fix the photobioreactor's orientation, and/or maintain the enclosed liquid medium at a substantially consistent thickness throughout its volume.

According to another aspect of the invention, particularly for embodiments involving photobioreactor systems including a plurality of individual, sealed, bag-like photobioreactor units, a handling system is provided for conveying large numbers of photobioreactor units along a path on a body of water. For example, a cable drive system may convey an enclosed photobioreactor unit on a path that extends from an output of a processing facility located on the edge of a body of water and along the surface of the body of water, and return the photobioreactor unit to an input of the processing facility.

Certain aspects of the invention are directed to photobioreactor designs and to methods and systems utilizing photobioreactors. A "photobioreactor," "photobioreactor unit" or "photobioreactor section" as used herein, refers to an apparatus or portion/segment thereof containing, or configured to contain, a liquid medium comprising at least one species of phototrophic organism and having either a source of light capable of driving photosynthesis associated therewith, or having at least one surface at least a portion of which is partially transparent to light of a wavelength capable of driving photosynthesis (i.e. light of a wavelength between about 400-700 nm). Many of the photobioreactor embodiments described herein comprise substantially enclosed photobioreactors, that is, photobioreactors which substantially separate the enclosed liquid and gas from liquid and gas of the environment external to the photobioreactor, as contrasted with an open bioreactor such as a pond or other open body of water, open tank or channel lacking a cover in which the liquid medium is freely exposed to the surrounding environment. An enclosed photobioreactor, photobioreactor unit or photobioreactor section may include inlets and/or outlets for gas, liquid, or both, and still be considered to be an enclosed photobioreactor. Furthermore, in the case where an enclosed photobioreactor unit is comprised of a plurality of individual photobioreactor sections connected in series, the individual photobioreactor sections in a disassembled configuration standing alone may not comprise an "enclosed" system; nevertheless, such photobioreactor sections are "enclosed photobioreactor sections" when assembled to form a photobioreactor unit, since the liquid and gas contained within the assembled photobioreactor unit and each photobioreactor section thereof is substantially separated from the environment external to the photobioreactor. A "sealed photobioreactor" is an enclosed photobioreactor that is substantially sealed from the outside environment for at least a certain amount of time and lacks gas and liquid inlets and outlets. For example, a large plastic tube or plastic bag may be charged with a liquid medium and carbon dioxide-enriched gas and then sealed to prevent any substantial transfer of liquid or gas in or out of the photobioreactor. Once growth of organisms within the sealed photobioreactor reaches a desired level and/or pollutant concentrations in the gas headspace reach a desired level, the sealed photobioreactor may be opened and the gas and/or liquid may be removed and exchanged.

The term "photosynthetic organism", "phototrophic organism", or "biomass," as used herein, includes all organisms capable of photosynthetic growth, such as plant cells and micro-organisms (including algae, euglena and lemna) in unicellular or multi-cellular form that are capable of growth in a liquid phase (except that the term "biomass," when appearing in the titles of documents referred to herein or in such references that are incorporated by reference, may be used to more generically to refer to a wider variety of plant and/or animal-derived organic matter). These terms may also include organisms modified artificially or by gene manipulation. While certain photobioreactors disclosed in the context of the present invention are particularly suited for the cultivation of algae or photosynthetic bacteria, and while in the discussion below, the features and capabilities of certain embodiments that the inventions are discussed in the context of the utilization of algae as the photosynthetic organisms, it should be understood that, in other embodiments, other photosynthetic organisms may be utilized in place of or in addition to algae. In general, certain embodiments of the invention may be designed to support the growth of unicellular, motile or sessile, flagellated or non-flagellated, phototrophic organisms that have volumetric yield rates which in certain embodiments may be greater than 0.2 g/L/day (dryweight), have total lipid contents which in certain embodiments may be greater that 20% (by mass) and cell sizes which in certain embodiments may range from 1 to 50 micrometer. For an embodiment utilizing one or more species of algae, algae of various types, (for example *Chlorella, Chlamdomonas, Chaetoceros, Spirulina, Dunaliella, Porphyridum, Hematococcus*, etc.) may be cultivated, alone or in various combinations, in the photobioreactor. Of course one or more of these and/or other algae types may be used in certain embodiments, for example, one or more of *Nannochloris* sp., *Tetraselmis chui* (strain PLY429), *Dunaliella salina, Pleurochrysis carterae, Tahitian Isochrysis* sp., *Rhodomonas salina, Pichochlorum oklahomensis, Pavlova lutheri, Phaeodactylum tricornutum, Tahitian Isochrysis, Nannochloris/Nannochloropsis, Nannochloris* sp., *Tetraselmis chui* (strain PLY429), *Skeletonema caustatum, Nannochloropsis oculata, Nannochloris* sp., *Nannochloropsis oculata, Chlorella minutissima, Nannochloris* sp., *Botryodopsis arhiza, Scenedesmus dimorphus, Heterococcus mainxii, Chlorella protothecoides, Ankistrodesmus braunii, Heterococcus brevicellularis, Monodus subterraneus, Scenedesmus dimorphus, Microspora* sp., *Nannochloropsis* sp., *Porphyridium* sp., *Chlorella* sp., *Neochloris oleoabundans, Chlorella vulgaris, Chlamydomonas acidophila, Spirulina platensis, Haematococcus lacustris, Aphanizomenon flos-aquae, Ankistrodesmusfalcatus, Botryococcus sudeticus, Coscinodiscus* sp., *Coscinodiscus wailisii, Nannochloropsis oculata, Dunaliealla bardawil, Dunaliella tertiolecta, Chaetocerous muelleri, Chaetoceros gracilis, Amphora* sp., *Amphora coffeaeformis, Ulva* sp., *Chlorella* sp., *Tetraselmis suecica, Spirulina platensis, Platymonas* sp., *Navicula lenzii, Chlamydomonas* sp., *Tetraselmis* sp., *Scenedesmus quadricuada, Chlorella sorokiniana, Selenastrum minutum, Chlorella sorokiniana*, and *Chlorella vulgaris*. In some embodiments using one or more species of macroalgae, macroalgae of various types, (for example *Chondrus, Porphyra, Palmaria, Laminaria, Ulva*, etc.) may be cultivated, alone or in various combinations, in the photobioreactor.

The phrases "at least partially transparent to light" and "configured to transmit light," when used in the context of certain surfaces or components of a photobioreactor, refers to such surface or component being able to allow enough light energy to pass through, for at least some levels of incident light energy exposure, to drive photosynthesis within a phototrophic organism.

In various embodiments disclosed herein, the methods and apparatus used to supply carbon dioxide-enriched gas and liquid medium vary depending on the nature of the system. Depending on the carbon dioxide content of the source gas, the volume of fresh gas used to support algae growth may be in the range of 0.1 to 10 cubic meters of gas per square meter of active growth area per day, with the higher values corresponding to the lower concentrations of carbon dioxide in the source gas. The source gas may be transferred to the photobioreactor with a large fan or a squirrel cage blower. The gas may be introduced at one end of the photobioreactor via a flexible gas seal or any suitable bulkhead, and may be vented at the opposite end via a similar sealed connection, or may be fed through a series of several photobioreactor sections connected end-to-end by flexible seals, before being vented. The venting apparatus may include a pressure regulator, for instance a weighted damper or baffle, that regulates the pressure in the photobioreactor to avoid distortion of the flexible lower barrier and/or damage to the structure.

In typical operation, the enclosed floating photobioreactors described herein may be operated in batch, semi-batch, or continuous mode, while sealed photobioreactors are typically operated in batch mode. Operation may be initiated by filling the photobioreactors with an inoculation culture containing the desired organism or organisms in aqueous solution containing suitable dissolved compounds and nutrients necessary to support desired growth. Agitation may be applied continuously or periodically to facilitate mixing and maintenance of organisms in suspension. The headspace above the liquid culture is filled with flue gas or another source of carbon dioxide, and the growth initiates upon exposure to sunlight. In batch mode, the culture grows from the initial charge of gas and liquid to the desired harvest density, whereupon some (e.g., one third of the culture) or all of the culture is harvested, the reactor is refilled, and the process is repeated. In some embodiments using a batch mode operation, harvesting and fresh liquid medium addition may occur simultaneously. In such embodiments, a floating divider may be used to divide the photobioreactor into two longitudinal portions in order to limit mixing at a liquid front that separates the liquid being harvested and fresh liquid medium being added. In semi-batch operation, a continuous or periodic flow of flue gas and/or nutrients or other compounds is added to maintain growth at desired rates for as long as possible before harvest. In continuous mode, once the liquid medium reaches the desired culture density, a steady outflow of culture is initiated from the reactor for harvest, and a matching flow rate of dilutant/nutrient liquid medium is introduced to make up for the harvest volume. In some embodiments, the reactor may be operated in a turbidostatic mode, where the harvest rate is modulated based on optical transmission measurements to maintain the desired culture density. Gas flow may be constant or variable based on time of day, pH, a direct measurement of dissolved carbon, and/or other parameters. Optionally, spargers may be used to increase the rate of transport of carbon dioxide into solution and/or to provide mixing of the liquid medium.

Finished culture at the desired harvest density may be drawn off an outlet end of the photobioreactor section with any suitable methods, such as with a flexible perforated pipe or hose and a centrifugal or other liquid pumping system. Bulkhead fittings may be used to form a connection for transferring liquid in and out of the photobioreactor. Liquid medium appropriate for the organism in culture may be optionally mixed with a portion of the harvested culture and introduced at an inlet end of the photobioreactor to replace harvested material and reseed the photobioreactor. This process may proceed on a continuous basis, or it may be operated in batch mode. In some embodiments, the inlet flow and the outlet flow are matched so as to maintain a substantially constant volume within the photobioreactor.

One embodiment of a floating photobioreactor section 100 is illustrated in FIG. 1. Liquid medium 101 is held within a tube 102 of flexible material, and gas, such as flue gas from a power plant, is held in a gas headspace 104 formed between liquid medium 101 and a cover section 106 of tube 102 that is at least partially transparent to light. Cover 106 may be constructed of thin, flexible material such that the application of a positive gas pressure to the interior of photobioreactor unit 100 "inflates" and supports cover 106 to form gas headspace 104. In the illustrated embodiment, cover 106 is optionally integrally formed with the lower portion of the tube containing the liquid medium 101. In some embodiments, a gas pressure of, for example, 0.10" water may be provided by a blower to support cover 106 to support the gas headspace.

With carbon dioxide-rich gas situated over liquid medium 101, carbon dioxide dissolves into the liquid medium, and algae within the liquid medium use the carbon dioxide and sunlight (or other light source) to photosynthesize, grow and reproduce, thereby producing biomass. The biomass, such as algae, in certain embodiments is harvested by removing the algae-rich liquid from the photobioreactor section.

In some embodiments, the carbon dioxide-rich gas and/or the liquid medium flow through photobioreactor section 100 at a controlled rate. In some embodiments, liquid medium flow is induced or enhanced with a paddle wheel, pump or other component configured to move liquid through the photobioreactor section. Mixing devices, described in more detail further below, may create liquid medium flow. In some cases, mixing devices may create an overall flow in one direction, while in other cases, local flow and mixing is created without an overall consistent flow of the liquid medium in a certain direction. In other embodiments, liquid medium flow is created by filling photobioreactor section 100 via the liquid inlet while simultaneously emptying photobioreactor section 100 via the liquid outlet. Gas flow may be created with fans, blowers, or the gas pressure present at the source of the gas, e.g., the output of a power plant.

Tube 102 may be sealed at the longitudinal ends such that a sealed photobioreactor unit comprising a "floating bag" is formed. In such an embodiment, the unit is operated in batch mode. Liquid medium and carbon dioxide-enriched gas is added to the photobioreactor unit and after a selected period of time, the liquid medium (including grown organisms) and the gas are removed, and new liquid medium and carbon dioxide-enriched gas is added. In other embodiments, tube 102 may be open at the longitudinal ends, which ends may be interconnected with either an inlet bulkhead or an outlet bulkhead, or may be interconnected with a longitudinal end of another photobioreactor section for embodiments involving multi-section photobioreactor units.

Tube 102 may be formed of any suitable transparent or translucent material, including a polymer film such as polyethylene, polypropylene, nylon, or polytetrafluorethylene, or a fabric material (coated, uncoated, woven or nonwoven). Other possible materials include polyethylene terephthalates, polyacrylate, polyvinyl chloride, polystyrene, and polycarbonate. Tube 102 may include a material which is UV stabilized and may, in certain embodiments be between about 25 to 250 microns in thickness, depending on the material. In other embodiments, tube 102 may include a material that is thinner than 25 microns or thicker than 250 microns. As can be appreciated, such materials are often substantially flexible and deformable.

Because different types of algae can require different light exposure conditions for optimal growth and proliferation, in certain embodiments, especially those where light-sensitive algal species are employed, light modification apparatus or devices may be used in the construction of the photobioreactors disclosed herein. Some algae species either grow much more slowly or die when exposed to ultraviolet light. If the specific algae species being utilized in the photobioreactor is sensitive to ultraviolet light, then, for example, certain portions of tube 102 (or other barriers disclosed herein) may be covered with one or more light filters that can reduce transmission of the undesired radiation. Such a light filter can readily be designed to permit entry into the photobioreactor of wavelengths of the light spectrum that the algae need for growth while barring or reducing entry of the harmful portions of the light spectrum. Such optical filter technology is already commercially available for other purposes (e.g., for coatings on car and home windows). A suitable optical filter for this purpose could comprise a transparent polymer film optical filter such as SOLUS™ (manufactured by Corporate Energy, Conshohocken, Pa.). A wide variety of other optical filters and light blocking/filtering mechanisms suitable for use in the above context will be readily apparent to those of ordinary skill in the art. In certain embodiments, especially for photobioreactors utilized in hot climates, as part of a temperature control mechanism, a light filter comprising an infrared filter may be used to reduce heat input into the photobioreactor system, thereby reducing the temperature rise in the liquid medium.

In many embodiments, tube 102 is formed of material that is substantially impermeable to gas and liquid, but in some embodiments, the material may be permeable or semipermeable to species and compounds of interest. In the embodiment illustrated in FIG. 1, tube 102 is free of longitudinally oriented seams and formed of a continuous material. In some embodiments, several of which are described further below, non-continuous component pieces may be connected together to form tube 102.

An anchor system 108 may include a single anchor to limit movement of photobioreactor section 100, or anchor system 108 may include several anchors to further restrict the orientation and motility of photobioreactor section 100. Anchor system 108 may be configured to be movable to enable it to agitate photobioreactor section 100 to increase diffusion of carbon dioxide into the liquid medium, increase suspension of organisms, and/or provide mixing of the liquid medium. In some embodiments, anchor system 108 may vibrate and/or oscillate tube 102.

The photobioreactor section may be anchored at suitable intervals to prevent excessive deflections and loss of the photobioreactor section. The intervals may be longitudinally spaced apart, for instance in the range of 5 to 20 meters, and the attachment may be for instance by means of tensioned cables or chains. The cables or chains may be attached to ground-holding anchors as are well known in the marine industry, or attached to the shore lines on either side of the body of water. The attachment angle of the anchoring system should be chosen so as to avoid excessive downward loads on the structure, which could cause variations in the culture depth, especially for embodiments in which tube 102 is formed of a substantially flexible and deformable material. Supplemental buoyancy may be used to offset the weight of heavy metal anchoring hardware. The photobioreactor also may be anchored edge-to-edge in parallel with adjacent photobioreactor sections, to the extent that the strength of the tubes allow this attachment, with only the edge-most photobioreactor sections attached to fixed anchor points.

Figure 2A:
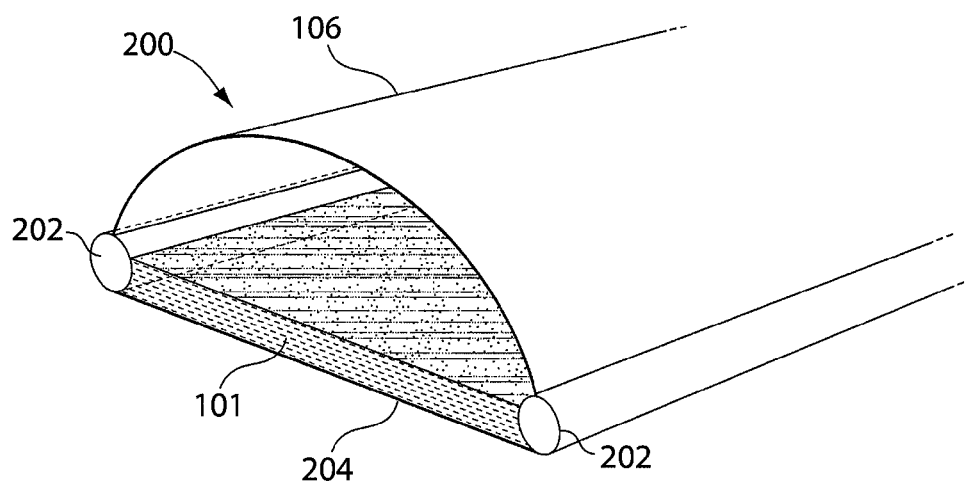
FIG. 2a is a perspective view of a floating longitudinal photobioreactor section according to another embodiment of the invention.
Figure 2B:
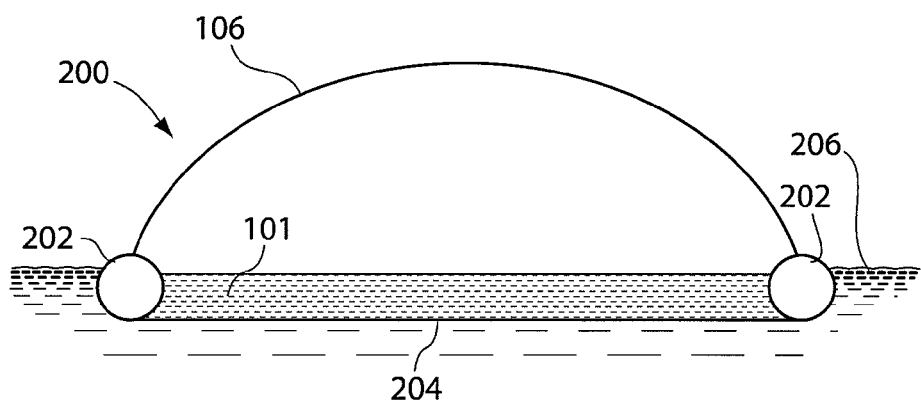

To aid in the floating of the photobioreactors on a body of water, according to one aspect of the invention, optional floatation elements 202 may be provided along the lateral edges of a photobioreactor section 200, as illustrated in FIGS. 2a and 2b. Floatation elements 202 may be continuous or periodic along the length of photobioreactor section 200.

In many embodiments, the vertical position of the floatation elements relative to lower barrier 204 defines a desired liquid medium thickness. When an appropriate amount of liquid medium is added to the photobioreactor section 200 to achieve the desired thickness, and lower barrier 204 is held substantially horizontal at or near the surface of the body of water 206, the liquid medium may be maintained at a substantially constant thickness (i.e. the liquid medium will have a substantially uniform depth) and the upper surface of the liquid medium can be maintained at or near the same level as the surface of a body of water 206. A lower barrier of a photobioreactor section is positioned at or near the surface of the body of water when the difference in the level of the upper surface of the liquid medium contained in the photobioreactor section differs from the level of the upper surface of the body of water by a distance that is no greater than the maximum depth of the liquid medium in the photobioreactor section. In certain embodiments, the lower barrier is held substantially horizontal at or near the surface of the body of water so that the difference in the level of the upper surface of the liquid medium contained in the photobioreactor section differs from the level of the upper surface of the body of water by a distance that is no greater than 50%, 40%, 30%, 20%, or 10% the maximum depth of the liquid medium in the photobioreactor section.

The horizontal dimension (width) of the flotation elements determines in part the stiffness with which the photobioreactor section assembly resists vertical loads and roll-wise moments (i.e. moments about a longitudinal axis of the photobioreactor section) applied to the assembly. In some embodiments, floatation elements 202 may have a diameter of between 8 cm and 30 cm, although any suitable dimensions may be used.

Floatation elements 202 may be part of a configuration in which a lower barrier 204 of photobioreactor section 100 is held in a substantially horizontal configuration from side-to-side, e.g. by optional tensioners as described in more detail below, along at least a portion of the length of photobioreactor section 200, and in certain embodiments the lower barrier 204 of photobioreactor section 100 is maintained, e.g., by tension applied by tensioners, so as to maintain a substantial portion of the area of the lower barrier in a substantially horizontal configuration. A substantial portion of the area of the lower barrier as used in the above context refers to at least 50% of the total wetted surface area of the lower barrier being maintained in a substantially horizontal configuration. In certain embodiments, at least 60%, 70%, 80%, 90% or at least 95% of the total wetted surface area of the lower barrier being maintained in a substantially horizontal configuration.

For purposes of the present application, a flexible material refers to a material that, without additional support structures, would substantially deform when subjected to forces which are typically encountered during typical operation of the apparatus. For example, in some embodiments, using a flexible material in the form of a thin layer of polyethylene or polypropylene for a lower barrier without tensioners or other support features would result in a lower barrier that would not remain in a substantially horizontal configuration when subjected to forces such as, for example, the weight of liquid medium within the photobioreactor, waves, or other movements of surrounding. As another example, in some embodiments, use of a thin layer of flexible plastic for a cover would result in a cover that would not support itself without the aid of support members or a positive gas pressure within the gas headspace of the photobioreactor. In some embodiments, various components or sub assemblies of the external envelop structure of the photobioreactors (such as a cover, end plates, or a lower barrier, etc.) may include some amount of non-flexible materials and still be considered a flexible material overall, so long as substantial levels of deformation of the overall structure would result during normal operation were it not for the presence of additional support structures. Thin, non self-supporting plastic films or sheets are examples of flexible materials that may be used according to certain embodiments of the invention.

By providing a substantially horizontal lower barrier 204, a liquid medium layer of substantially uniform depth may be maintained within photobioreactor section 200. A substantially uniform thickness (depth) of the liquid medium layer means a thickness which varies by 50% or less across an area or cross-section of interest. In certain embodiments, the thickness which varies by 40% or less, 30% or less, 20% or less, or 10% or less. In embodiments where the thickness is substantially constant from side-to-side within a photobioreactor section, the liquid medium layer thickness may decrease substantially (i.e., by more than 50%), but only at the extreme edges of the photobioreactor section (e.g., where the lower barrier connects to floatation element) and the liquid medium layer still may be considered to have a substantially uniform depth which extends from approximately the first floatation element across the width of the photobioreactor section to approximately the second flotation element positioned on the opposite side of the photobioreactor section. In certain embodiments, the liquid medium may have a substantially uniform depth from approximately the first floatation element across the width of the photobioreactor section to approximately the second flotation element positioned on the opposite side of the photobioreactor section over a substantial portion of the length of the photobioreactor section and/or area of the lower barrier of the photobioreactor section; for example over at least 50%, 60%, 70%, 80%, 90%, or 95% of the total length/area.

As some specific examples, in some embodiments, the liquid medium layer of substantially uniform thickness of 20 cm may vary by approximately 3 cm (or less or more than 3 cm) from side-to-side within the photobioreactor section. A substantially constant thickness liquid medium layer may help to improve the efficiency of biomass production within the liquid medium. For example, at a thickness of approximately 20 cm or less, sunlight may penetrate the entire liquid medium layer in some embodiments. Thicknesses less than 20 cm, for example a thickness of approximately 2 cm, 5 cm, or 10 cm, may be used in some embodiments. The use of smaller liquid medium thicknesses may reduce energy usage with respect of moving liquid medium, and may facilitate the production of higher biomass concentrations in the liquid medium. Because larger liquid volumes may increase the energy used and/or cost of harvesting biomass, higher biomass concentrations may facilitate more efficient harvesting.

Floatation elements 202, which may be formed from a wide variety of buoyant materials, for example closed-cell foam or air-filled plastic tubing, or any other suitable buoyant materials, also may be used to control or contribute to controlling the shape of the photobioreactor section and/or maintain the orientation of the photobioreactor section.

In some embodiments, photobioreactor section 200 may be approximately 1 to 10 meters wide. For embodiments in which a single photobioreactor section 200 forms a continuous photobioreactor unit of a photobioreactor system (i.e. is not serially interconnected with other photobioreactor sections to form a multi-section photobioreactor unit), the overall photobioreactor section 200 may be a suitable length to process a desired amount of carbon dioxide and/or produce a desired rate of biomass production. In general, the photobioreactor unit length will exceed the width of the photobioreactor unit, and the ratio of length to width may be greater than 10:1, greater than 100:1, and may exceed 1000:1. The gas containing elevated concentrations of carbon dioxide (i.e., carbon dioxide concentrations which are higher than ambient air) may range from 1%-100% wt., but typically in the range of 4%-20% wt. In some embodiments, the operating pressure of the reactor may be substantially equal to or only slightly higher than that of the surrounding atmosphere to limit imparting curvature to the lower barrier and creating depth variation of the liquid medium. Gas flow rates may likewise be maintained to limit pressure differences axially along the length of a photobioreactor unit. Flow rates of the gas for certain continuous or semi-batch systems may generally range from about 0.05-0.5 cm/sec, or other suitable flow rate. Liquid flow rates for certain continuous or semi-batch systems may generally range from about 1-100 cm/sec. Biomass concentrations generally may range from 0.01-10 g/l. The above ranges are provided as examples only, and any suitable values may be used depending on particular circumstances.

Cover 106 may be constructed from a wide variety of transparent or translucent materials, including flexible materials, such as the materials listed above with reference to tube 102 illustrated FIG. 1. Alternatively, cover 106 may be formed from glass or resin-supported fiberglass or other rigid, self-supporting material. In certain embodiments, cover 106 in combination with support elements, is sufficiently rigid to be self-supporting and to withstand typical expected forces experienced during operation without collapse or substantial deformation. Portions of cover 106 may be non-transparent in certain embodiments, and such portions can be made out of similar materials as described above for the at least partially transparent portions of cover 106, except that, when they are desired to be non-transparent, such materials should be opaque or coated with a light-blocking material.

The material of cover 106, in certain embodiments in combination with support elements, may be designed to support external loads such as snow, wind and/or negative pressures applied by an induced-draft fan. Additionally, in some embodiments, cover 106 may be able to withstand internal positive pressure, such as when a forced-draft fan is used to push gas through the photobioreactor.

Cover 106 is shown in cross section as a semicircle or other curved surface in many of the embodiments disclosed herein, however, any suitable shape may be used, including a rectangular, triangular or trapezoidal shapes.

Component pieces, such as cover 106 and lower barrier 204, may be integrally formed or connected to each other or to floatation elements 202 by thermal or RF welding, a stitched seam, a mechanical clasp, adhesives, or any other suitable method.

Lower barrier 204 may be made of the same or similar material as cover 106. In certain embodiments, it may be made of a stronger (at least in tension) material than cover 106, such as rubberized fabric, waterproof tarpaulin material, or commercial pond liner. Lower barrier 204, in certain embodiments, need not be light transparent The quantity of algal culture and initial population density of algal species may be chosen in consideration of the desired growth period, expected growth rate, and illumination levels, as would be apparent to those skilled in the art. The optimum culture depth is known to be a function of population density, based on the most favorable average light levels for efficient growth. Accordingly, liquid medium depth may be selected based at least in part on desired population density. The nutrient levels may be manipulated so as to induce biological stresses on the organisms in order to increase the production of certain desired compounds during the growth cycle. The quantity and carbon content of the gas feed may be chosen based at least in part on the expected conversion efficiency and desired quantity of biomass. If a relatively dilute carbon source (such as flue gas from a gas turbine power generation station) is used, a relatively large volume of gas may be used, while a photobioreactor fed a concentrated carbon source such as flue gas from a coal-burning plant or exhaust from a fermentation facility may use a relatively smaller volume of gas.

While some of the embodiments described herein may employ the movement of liquid through a gas headspace to promote mass transfer between the gas and liquid, in certain embodiments, additionally or alternatively, gas may be sparged into the liquid. For example, while the bulk of gas distribution into the liquid medium present in a photobioreactor unit may be through the liquid interface with a gas headspace, a not insignificant amount of gas may be sparged into the liquid medium in certain embodiments. The sparging, in addition to creating an additional gas-liquid interface, may create turbulence or additional turbulence in certain regions where such turbulence is desirable. Further description of the role of turbulence may be found in U.S. Published Application No. 2005/0260553 which is herein incorporated by reference in its entirety.

In some cases, particularly when a source of cold water is available (e.g., a nearby river, aquifer, or ocean) and/or a source of warm water is available (e.g., waste heat heated water from a power plant or industrial process), it may be advantageous to provide active thermal control to the photobioreactor. Active thermal control may be provided by including a channel beneath the lower barrier of the main channel which carries the liquid medium. Water of a selected temperature may then be supplied at a controlled rate and/or temperature to the channel below the barrier to heat or cool the liquid medium. By including active thermal control, temporal variation of temperature may be more precisely controlled. Such control may be useful for maintaining advantageous growth conditions or may allow thermal excursions to lower temperatures at night to control populations of parasitic species.

Figure 3:
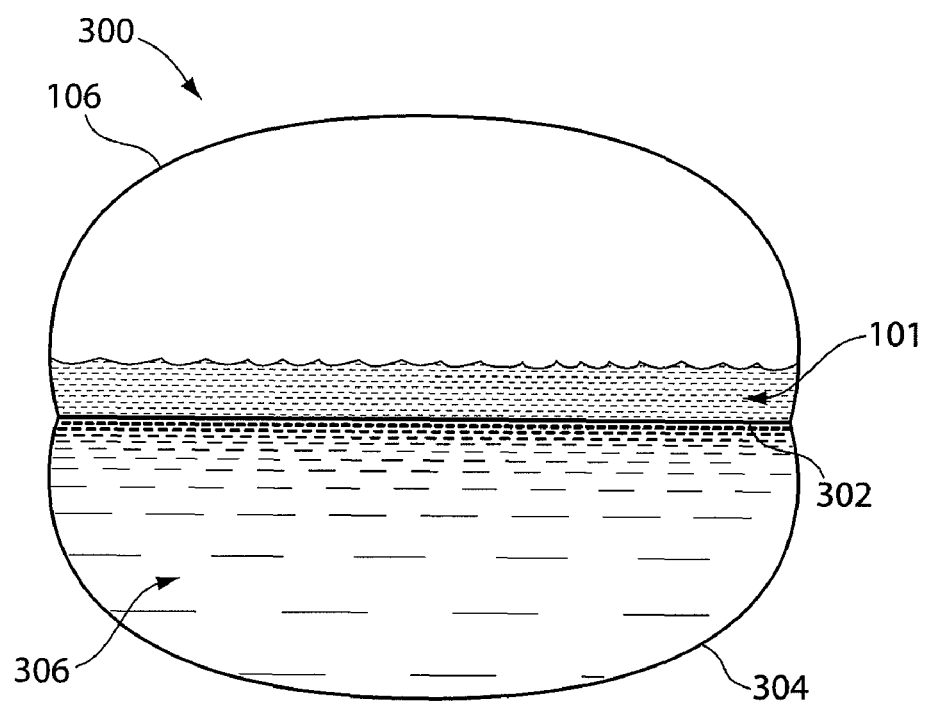
FIG. 3 is a cross-sectional view of a longitudinal photobioreactor section according to another embodiment of the invention.

A photobioreactor section 300 including an internal divider which acts as a support for liquid medium is provided in one embodiment, as illustrated in FIG. 3. In this embodiment, a divider 302, which may be formed of flexible material, provides a substantially horizontal lower barrier upon which liquid medium layer 101 may be supported. A second barrier 304 forms a second channel 306 below the liquid medium. Divider 302, cover 106 and second barrier 304 may be constructed and arranged to act as a tensioner, such that tension is applied to divider 302 by horizontal outward pressure on cover 106 and/or second barrier 304.

In embodiments where active thermal control is desired, divider 302 may be made of a thermally conductive material and/or a thin material. Water, or other liquid, may be provided in second channel 306 to control the temperature of liquid medium 101. In some embodiments, water may be continuously flowed through second channel 306, while in other embodiments, water may be provided to second channel 306 in a batch mode. The water supplied to second channel 306 may be water containing waste heat from an industrial process, such as the industrial process that creates the carbon-dioxide enriched gas, or chilled water (i.e. water below ambient temperature).

To provide an outward force on the edge supports to tension lower barrier 204, and/or to support cover 106, tensioners in the form of arcuate members, such as arch elements, may extend between the edge supports at intervals along the length of the photobioreactor assembly. The arch elements may be bent into a configuration where they are bent more than they would be in a relaxed state, and therefore they exert an outward force on the edge supports to provide a tension on lower barrier 204. The arch elements, or other tensioners, by applying lateral tension to the lower barrier serve to maintain the lower barrier in a substantially horizontal configuration and enable the lower barrier to resist deformation forces applied by the weight of the liquid media and external forces applied to the photobioreactor segment by the body of water on which it is floating (e.g. by wave action, etc.) and/or other forces applied to the photobioreactor segment. The maintenance of a substantially horizontal lower barrier, in turn, facilitates the ability to provide and maintain a substantially constant depth of liquid medium across the width and along the length of the photobioreactor segment.

Figure 4:
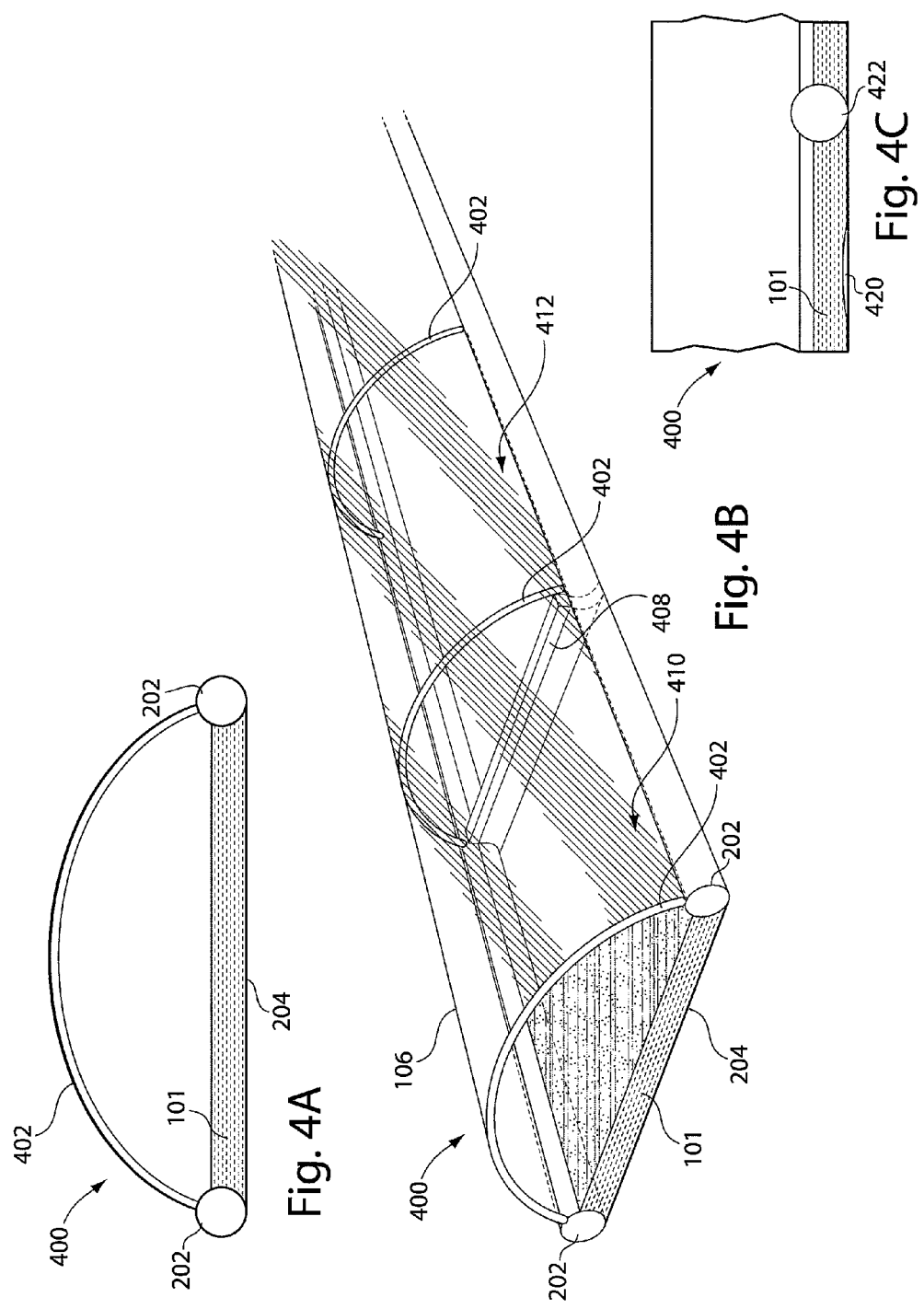

One embodiment of a photobioreactor 400 employing arch elements 402 is illustrated in FIGS. 4a and 4b. The arch elements may be attached to the edge supports by means of sockets, flanges, slots, pockets provided on the edge supports, simply penetrating the ends of the arch elements into the material of the edge supports or by any other suitable means. In certain embodiments, lower barrier 204 provides an inward force that holds the arch elements to the preferred curved shape. The arch elements may be formed of a light, stiff, inexpensive, corrosion-resistant material such as polymer (PVC, polycarbonate, polypropylene, polyethylene, nylon, etc), fiber-reinforced composite polymer, recycled polymer, aluminum or coated steel, pultruded composite such as fiber-glass, wood, or wood/polymer composite. The upper surface of arch elements 402 may be smooth and possibly curved to prevent damage to cover 106. The cross-sectional shape of the arch elements may be chosen to balance among the objectives of efficient material utilization, reduced shadowing of the algal culture, and ease of attachment to the edge supports. In some embodiments, a cylindrical PVC pipe approximately one inch in diameter may be used as an arch element with a photobioreactor section having a width of approximately two meters.

A longitudinally movable divider 408 may be included for use in semi-batch mode. Moving divider 408 may be used to maintain a division of the photobioreactor into two longitudinal portions 410, 412 in order to limit mixing at a longitudinally progressing liquid front that separates the liquid being harvested and fresh liquid medium being added. Divider 408 may be free-floating or operably connected to floatation elements 202, edge supports (described below) or other components of the photobioreactor. Divider 408 may comprise a floating element or be of any other suitable construction.

In some embodiments, as illustrated in FIG. 4c, selectively deployable dividers may be used to isolate regions of a photobioreactor unit. By isolating one or more regions of a photobioreactor unit from an adjacent region, the photobioreactor unit can be, for example, configured for sequential amplification of organisms within the liquid medium. The selectively deployable dividers may be in the form of inflatable/deflatable dividers 420, 422, dividers that are movable into and out of the liquid medium, and/or any other suitable divider design that can be deployed and removed. In FIG. 4c, divider 420 is shown deflated, while divider 422 is inflated, or deployed.

In some embodiments, the selectively deployable dividers may be controlled automatically or manually in response to the amount of algae or other organisms present in the liquid medium. For example, optical density of the liquid medium may be measured, and the selectively deployable divider may be deployed or removed in response. Similarly, in some embodiments, divider 408 of FIG. 4b may be controlled automatically in response to optical density measurement of the liquid medium.

Figure 5:
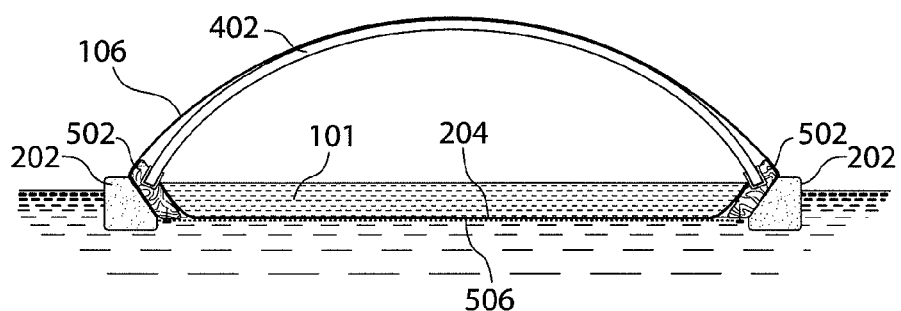
FIG. 5 is a cross-sectional view of one embodiment of a photobioreactor section having edge supports according to one embodiment of the invention.

In some embodiments, in addition to floatation elements 202, additional edge supports may be provided. As shown in FIG. 5, edge supports 502 may extend along the lateral sides/edges along the length of the photobioreactor section and may be configured and positioned to provide an interface between cover 106 and lower barrier 204. Edge supports 502 may be formed of a rigid material such as formed metal (e.g., galvanized steel), extruded metal (e.g., aluminum), extruded polymer (e.g., glass-filled nylon or polypropylene), extruded foamed polymer, extruded recycled polymer, wood, or extruded wood/polymer composite, etc. Edge supports 502 may have a cross-sectional shape which is dictated by a standard building material shape, such as the shape of dimensional lumber, for example a cross-section 1 inch thick by 5.5 inches wide, or they may have a custom shape tailored specifically to the application. For example, an L, C, Z, O, or box profile may be utilized to add stiffness, and grooves, slots, and/or other features may be included to facilitate attachment of lower barriers, flotation elements, and/or arch elements or other tensioners. The distance between the edge supports, defining the effective width of the photobioreactor section, may be selected or adjusted to suit the application, but may for instance be in the range of 1 to 10 meters. The edge supports may also be provided with features such as slots or grooves to facilitate the attachment and sealing of the cover and the lower barrier to the edge supports, to prevent influx of air, rainwater, pond water, or other contaminants and efflux of flue gas or liquid medium. In some embodiments, cover 106 and lower barrier 204 are sealed to the edge supports by insertion of elastomeric cords into a pair of dovetail grooves; the cords force the barrier films against the inner surfaces of the dovetail slots, creating a tight seal (not illustrated). In some embodiments, such as the embodiment illustrated in FIG. 10 (described further below), edge supports 502 may include an enclosed void or be made of a buoyant material serving the function of the floatation elements 202.

A support element, such as a support mesh 506, may be provided as part of lower barrier 204 to support the flexible material of lower barrier 204. Support mesh 506 may be constructed and arranged such that as edge supports 502 are pushed apart by arch elements 402, support mesh 506 is pulled taut before the flexible material of lower barrier 204 reaches a point of tensile failure. In this manner, support mesh 506 provides a horizontal support structure for the flexible material of lower barrier 204, and may carry the bulk of the tension applied by the arch elements such that the flexible material of lower barrier 204 may not be required to be as resistant to tension as in an embodiment where only the flexible material itself is tensioned by edge supports 502 in combination with the arch elements. Of course, other support elements, such as cords, ropes, lines, polymer, metal wire, fiber or any other suitable support elements may be used to resist the outward forces applied by the arch elements. In some embodiments, a rigid or semi-rigid material may be used to form lower barrier 204 and provide a flat bottom (and thereby a substantially constant liquid medium depth) without the use of edge tension.

Figure 6A:
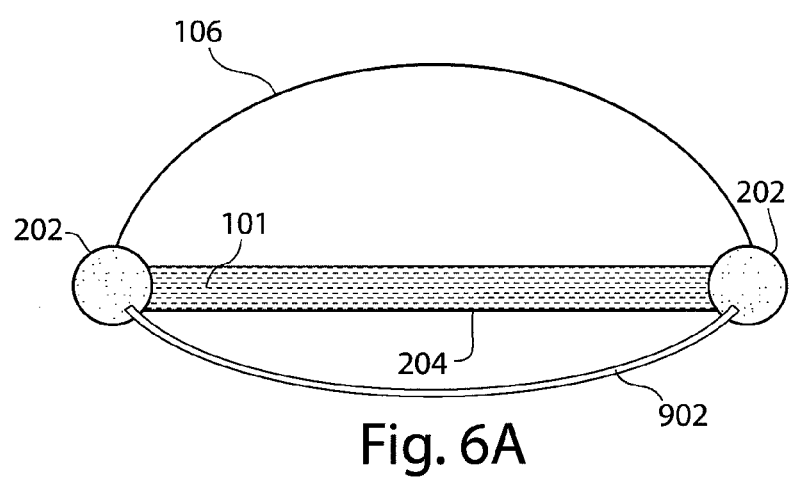
FIG. 6a is a cross-sectional view of a longitudinal photobioreactor having tensioners according to another embodiment of the invention.

As shown in the embodiment illustrated in FIG. 6a, instead of arch elements that extend over the liquid medium, as illustrated in FIGS. 4a and 4b, tensioners in the form of transverse spars 902 may be provided underneath lower barrier 204 to provide an outward force on floatation elements 202 (and/or edge supports in some embodiments). For example, as shown in FIG. 6a, an arcuate transverse spar 902 is inserted into floatation elements 202. Multiple transverse spars may be provided along the length of a photobioreactor section. In such an embodiment, cover 106 may be held aloft by positive gas pressure within the photobioreactor, or by arch elements that provide little or no tensioning function.

In other embodiments (not illustrated), spars 902 may be straight instead of arcuate. For example, straight spars having a length that is slightly exceeds the relaxed width of lower barrier 204 may extend from one floatation element 202 to the other floatation element above and/or below lower barrier 204. The length of the spars (straight or arcuate) may be controllable in some embodiments which may facilitate control of the tension applied to lower barrier 204. For example, telescoping spars may be connected to the floatation elements (or edge supports).

Figure 6B:
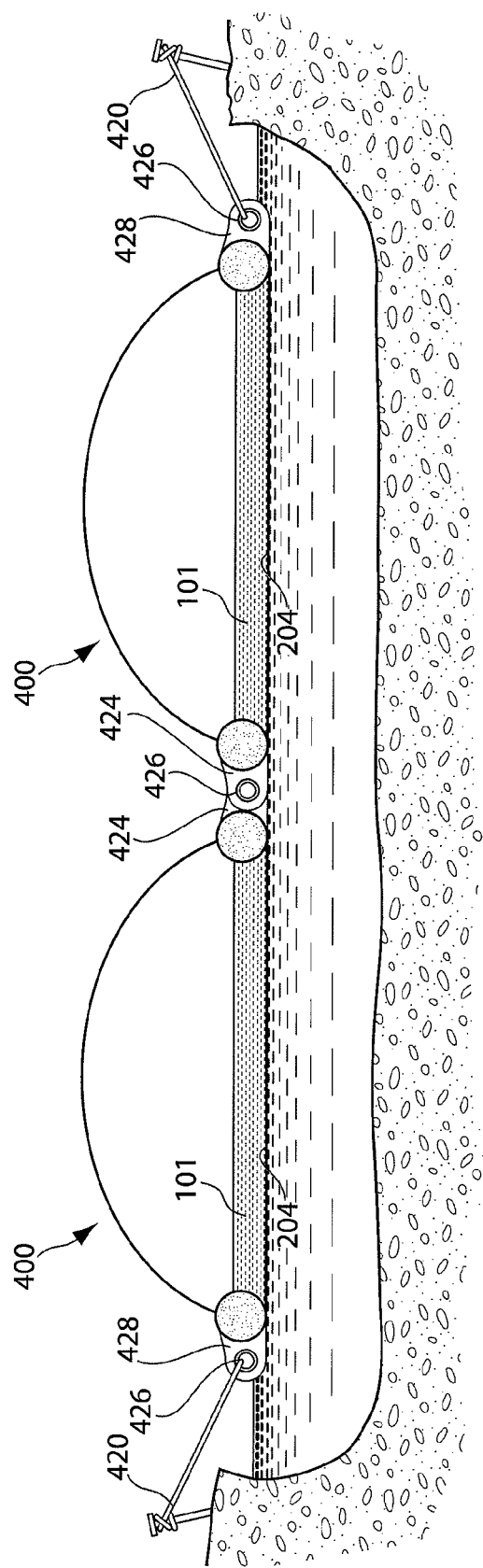
FIG. 6b is a cross-sectional view of two interconnected photobioreactor sections employing tensioning elements tethered to the shore according to another embodiment of the invention.

According to certain embodiments of the invention, lower barrier 204 may be tensioned by applying tension to the sides of a photobioreactor unit with tensioners comprising cables, chains, ropes or other tensioners which are anchored to the a solid surface that is external to the photobioreactor, for example, the shore of the water body on which the photobioreactor is positioned, and/or the bed of the water body. As shown in FIG. 6b, two photobioreactor units 400 may be positioned adjacently and substantially parallel to each other, and the photobioreactor units may be attached to each other along lateral sides of the photobioreactor units such that the tension applied by cables 420 is applied to each lower barrier 204. In embodiments where three or more photobioreactor units are positioned adjacently and substantially in parallel, some photobioreactor units are attached to two adjacent units positioned on either lateral side of such photobioreactor unit (e.g. a middle photobioreactor unit of a group of three).

Any suitable method of securing a photobioreactor unit to an adjacent photobioreactor unit may be used, but in certain embodiments, each photobioreactor unit 400 has a sleeve 424 that can be intertwined, intercalated, enmeshed, etc. with a sleeve of the adjacent photobioreactor unit, as described further below with reference to FIG. 6c. A pipe 426, or other longitudinal element (e.g. rod, which may, in certain embodiments be constructed to be sufficiently buoyant to act as floatation elements) is passed through the sleeves 424 of each photobioreactor unit, thereby interconnecting the units and allowing tension created by cables 420 to be applied to adjacent units.

The photobioreactor units that have sides which are directly anchored to shore may include a sleeve 428 that, optionally, is configured differently from sleeve 424 in that it is not configured to facilitate interconnection with an adjacent photobioreactor unit, but instead is configured for connection to cables 420. Pipes 426 (or rods, which may, in certain embodiments be constructed to be sufficiently buoyant to act as floatation elements) may be inserted into sleeve 428 and one or more cables 420 may be attached to pipes 426. Of course, in some embodiments, the photobioreactor units that are directly anchored to shore may not include sleeves, and instead include other features for connections to cables 420, such as grommets, hooks, rings, tie-downs, winches, or other features.

Figure 6C:
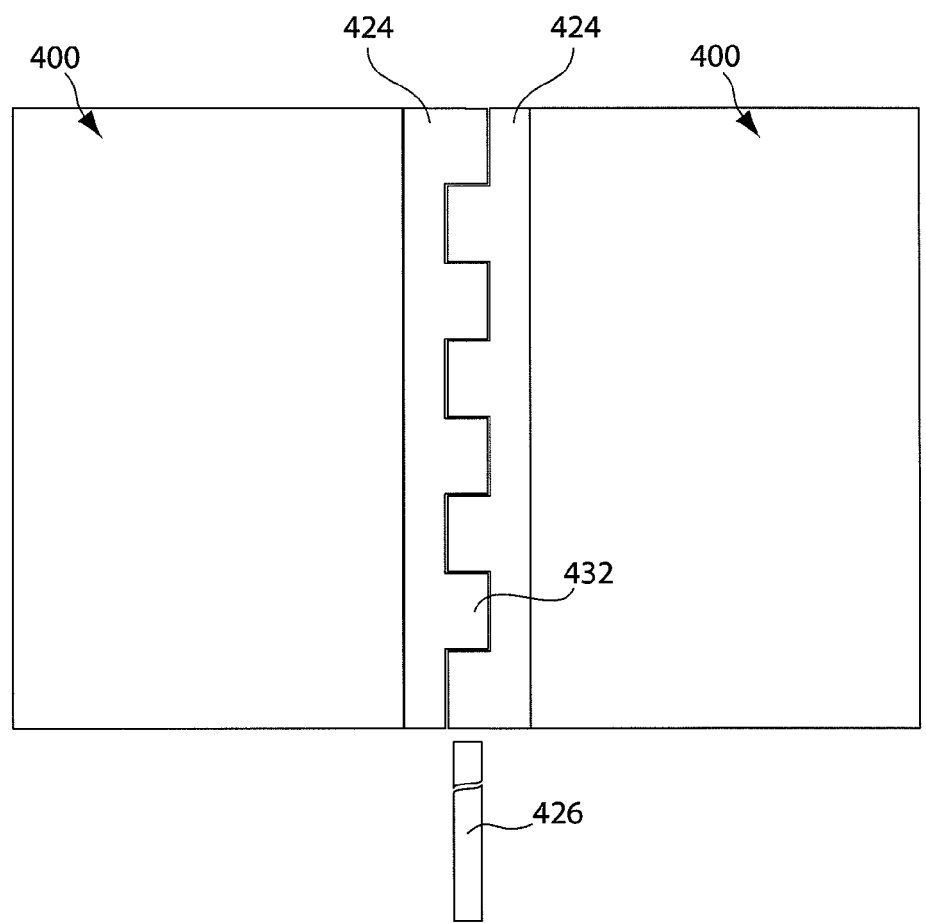
FIG. 6c is a top view of an arrangement for connecting photobioreactor sections in parallel to each other.

One example of a method of interconnecting adjacent photobioreactor units is illustrated in FIG. 6c. In this embodiment, each sleeve 424 includes regularly spaced gaps into which corresponding projections 432 of the adjacent sleeve are inserted. Pipe 426 is then inserted through the intertwined sleeves 428. In some embodiments, the gaps and corresponding projections may be, for example, one foot in length.

Figure 6D:
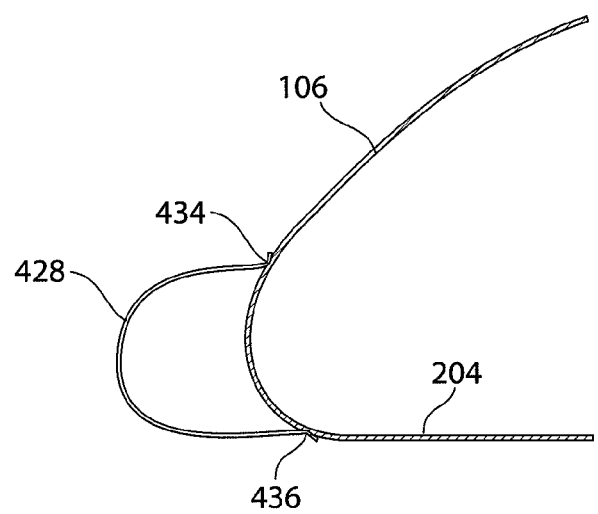
FIG. 6d is a front cross-sectional view of a sleeve attached to a side of a photobioreactor section according to one embodiment of the invention.

As illustrated in FIG. 6d, sleeves 428 (and/or 424) may be welded to the barrier film that forms cover 106 and lower barrier film 204 at an upper weld 434 and a lower weld 436. The size of sleeves 428/424 may be selected based on the size of pipe 426 to be used, and in some embodiments, sleeves 428/424 may have a cross-sectional arc length of approximately twelve inches, and the arc length of the barrier film may be five inches between upper weld 434 and lower weld 436.

Pipes 426 may be open at the ends to allow water from the supporting water body to enter the pipes so that the overall buoyancy of the pipe assemblies is limited. In other embodiments, pipes 426 may be capped at their ends to provide buoyancy. In still other embodiments, other connection elements may be used, such as solid rods, or tubes constructed from buoyant material.

Other suitable connection arrangements may be used, including arrangements that do not use sleeves. As some examples, adjacent photobioreactor units may be attached to each other with cables, a continuous length or discontinuous segments of hook and loop fastener, welds between materials of each unit, adhesive bonding, etc.

Figure 7:
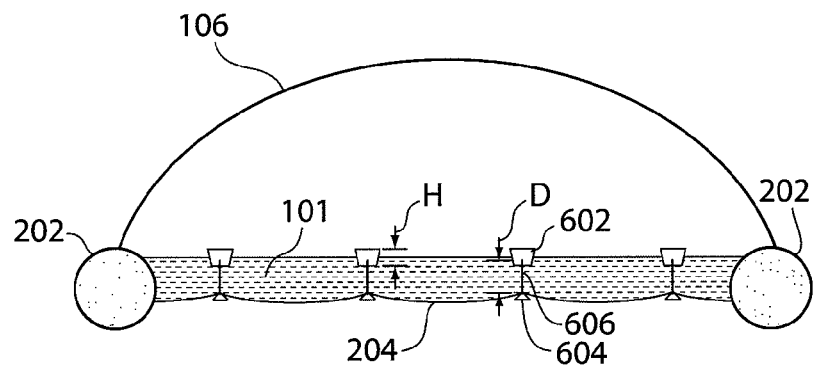
FIG. 7 is a cross-sectional view of a photobioreactor section including float supports for supporting the lower barrier, according to one embodiment of the invention.

In an alternative embodiment, instead of using tension to hold lower barrier 204 in a substantially horizontal position, distributed bobber/sink pairs may be used to hold lower barrier 204 in a substantially horizontal position and maintain a relatively constant thickness of liquid medium. For example, as shown in FIG. 7, a plurality of bobbers 602 and sinks 604 form lower barrier support pairs across the photobioreactor. Each sink has a density in excess of that of the liquid medium and is attached to lower barrier 204. Attached to each sink is a floating bobber with a density less than that of the liquid medium. Each sink is connected to each bobber with a tether 606 or rod with characteristic length D corresponding to the desired liquid medium depth. If the local film depth is less than D, the float/sink combination applies a net downward force on the lower barrier film. If the local film depth exceeds D, the bobber/sink pair exerts a net upward force on the lower barrier. Thus, the distributed bobber/sink pairs act to equalize the depth of the liquid medium. The range of depths over which this effect occurs corresponds roughly to the vertical extent H of bobber 602.

Figure 8:
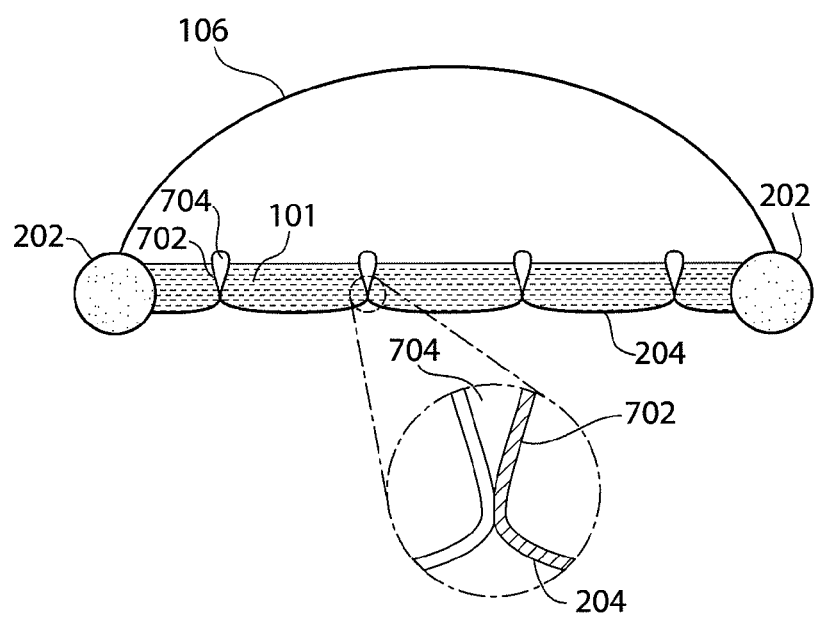
FIG. 8 is a cross-sectional view of another embodiment of float supports for supporting the lower barrier of a photobioreactor section.

Another alternative embodiment for controlling liquid medium thickness is illustrated in FIG. 8. In this embodiment, lower barrier 204 includes linear ribs 702 formed by folding and seam welding the lower barrier material and filling a resulting interior volume 704 with foam, compressed air, or other buoyant material. Ribs 702 exert a depth-dependent force on the lower barrier, thereby serving to maintain the thickness of the liquid medium.

In some embodiments, lower barrier 204 may be constructed of a material that includes a multiplicity of integral inflated air pockets, similar in appearance to "bubble wrap" packing material. The inflated air pockets may be evenly distributed across the lower barrier, or, in some embodiments, specific sections may have a greater surface density of inflated pockets and/or different sizes of inflated pockets.

In certain embodiments, tubular floatation devices may be attached to lower barrier 204 (either above or below the barrier) to control or maintain liquid depth. The tubular floatation devices may be constructed of closed-cell foam, or any other suitable material.

Figure 9:
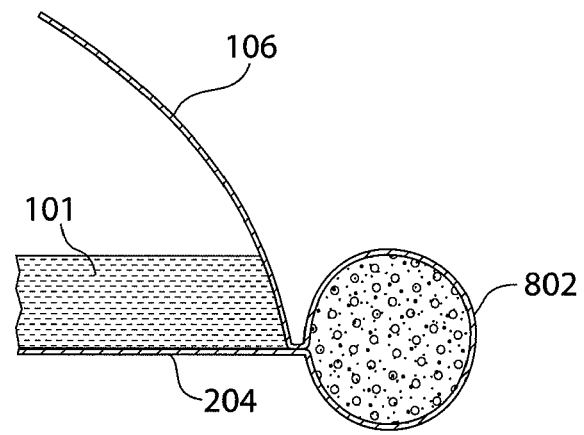
FIG. 9 is a cross-sectional view of an embodiment of floatation elements for supporting a photobioreactor section.

FIG. 9 illustrates an alternative embodiment in which a continuous barrier film (forming both cover 106 and lower barrier 204) is modified to include integral floatation elements. The barrier film is continuously welded lengthwise using thermal, sonic, ultrasonic, or RF welding (or other suitable sealing methods) along the edges to form lengthwise floatation tubes 802. The floatation tubes may be filled with buoyant foam in some embodiments. In some embodiments, photobioreactor sections may be interconnected in parallel and floatation elements (such as floatation tubes 802) may be provided only on the outermost photobioreactor sections to provide tension to the lower barrier. In other embodiments, other tensioners, such as arch elements, may span laterally across multiple photobioreactor sections that are interconnected in parallel.

Figure 10:
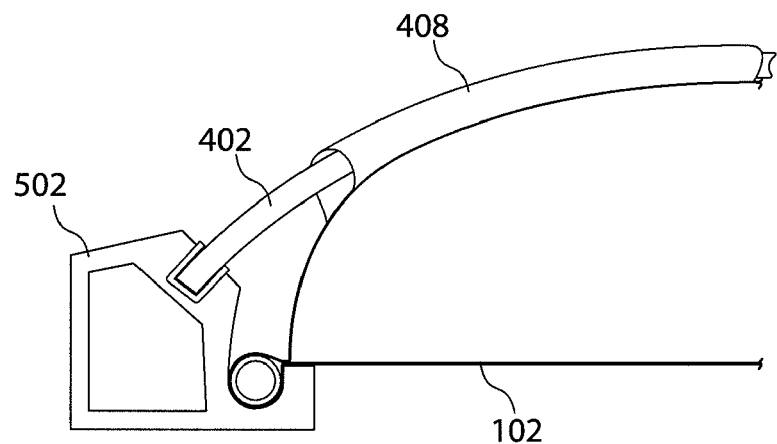
FIG. 10 illustrates an embodiment including arcuate members that support a cover of an enclosed photobioreactor.

For certain applications, it may be desirable to combine a continuous barrier film construction (i.e. one continuous, sheet forming both cover 106 and lower barrier 204) with external mechanical support for the cover. FIG. 10 illustrates an embodiment including hollow buoyant edge supports 502, arch members 402, and a continuous barrier film construction tube 102. The arch members are external to tube 102, and the tube is attached to the arch members with sleeves 408 welded across the upper surface of the tube at longitudinal intervals. Alternatively, arch members 402 may be attached to tube 102 by adhesive, stitched seam, or other suitable methods.

Referring to FIG. 11a, in certain embodiments, liquid medium agitation/movement is accomplished or enhanced by employing mixing elements, such as mixing bars 1102, placed within the photobioreactor section at intervals along the length of the photobioreactor sections. As illustrated in FIG. 11a, mixing bars 1102 may be arranged perpendicularly to the longitudinal axis of the photobioreactor section. In this embodiment, mixing bars 1102 are pulled back and forth along at least a portion of the length of the photobioreactor section by one or more cables 1104 which are actuated by a drive mechanism 1106. The size, shape and buoyancy of the mixing bars, and the speed, length, and frequency of the drive motion may be selected to provide desired mixing/flow inducement while constraining the overall energy input into the system. The mixing bars may be configured so as to avoid damage to lower barrier 204 in case of rubbing between the mixing bars and the lower barrier 204. In one embodiment, the mixing bars are made of closed-cell polyurethane foam of substantially circular cross-section and of approximately 3 inches diameter and 6 inches long, pressed at intervals onto a stainless steel tube extending approximately 80 percent of the width of the photobioreactor section.

According to some embodiments, a dual motor system is used to move mixing bars along the length of a photobioreactor section. As illustrated in FIG. 11b, drag boards 1110 are used as mixing elements, and are attached to a cable 1112. Cable 1112 is connected to two opposed motors 1114a and 1114b, in some cases via one or more pulleys 1116. Motor 1114b pulls drag boards 1110 along a length of the photobioreactor section in one direction, and then motor 1114a pulls drag boards 1110 along the length photobioreactor section in the opposite direction.

In other embodiments, a single motor may be used in combination with an energy storage unit such as a spring. In certain such configurations, the system is configured so that as the motor pulls the drag boards (or other mixing elements) in one direction, the motor also operates on the energy storage unit. When the motor has finished pulling the drag boards in one direction, the energy storage unit pulls the drag boards in the opposite direction.

Figure 12A:
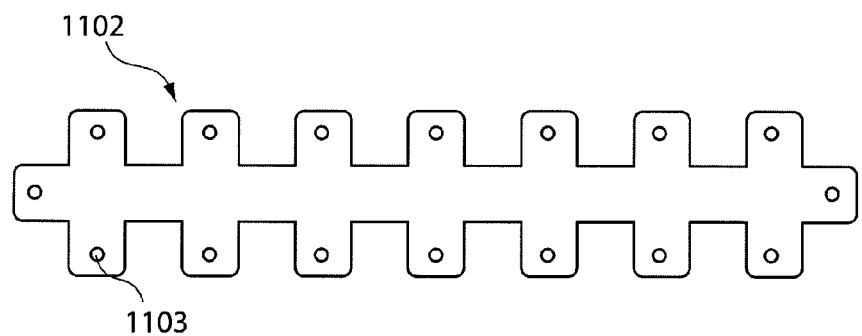
FIG. 12a is a front view of a mixing element according to one embodiment of the invention.

In some embodiments, the mixing bars may be corrugated cylinders constructed from blow-molded plastic. For example, as illustrated in FIG. 12a, a hollow mixing bar 1102 may be vacuum formed from thin-walled plastic, and the outer diameter of the mixing bar may vary in size periodically. Perforations 1103 may optionally be included to permit mixing bar 1102 to be filled with liquid medium. The mixing bars may be driven by means of a pair of stainless steel cables, attached by clamps to the mixing bars, and driven by motorized drive spools 1108 at the ends of the photobioreactor section or photobioreactor unit. In certain embodiments, the mixing bar may be constructed of materials that render it positively buoyant by 20%-70%, in order to provide substantial interaction with the liquid medium while limiting or avoiding contact with the lower barrier to prevent damage to the lower barrier. In some embodiments, the mixing bars have lengths that extend across at least approximately 80% of the width of the photobioreactor unit in which they are positioned. In some embodiments, the mixing bars have heights that allow penetration well into the liquid medium (e.g. at least 80% of the depth of the liquid medium).

Figure 12B:
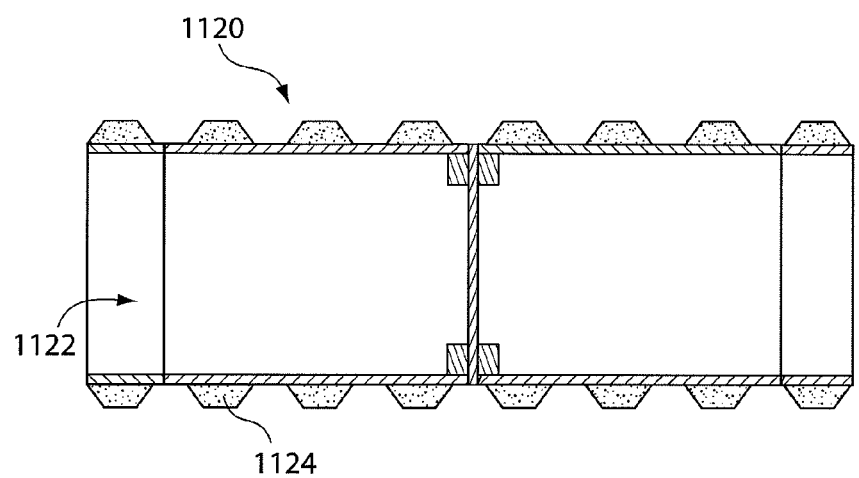
FIG. 12b is a cross-sectional side view of a mixing element according to another embodiment of the invention.

Another embodiment of a mixing bar 1120 is illustrated in the cross-sectional view of FIG. 12b. In this embodiment, mixing bar 1120 includes a hollow cylinder 1122 and trapezoidal protrusions 1124 disposed on the exterior of cylinder 1122. In some embodiments, commercially available swim barrier buoys may be used as mixing bars.

Figure 13:
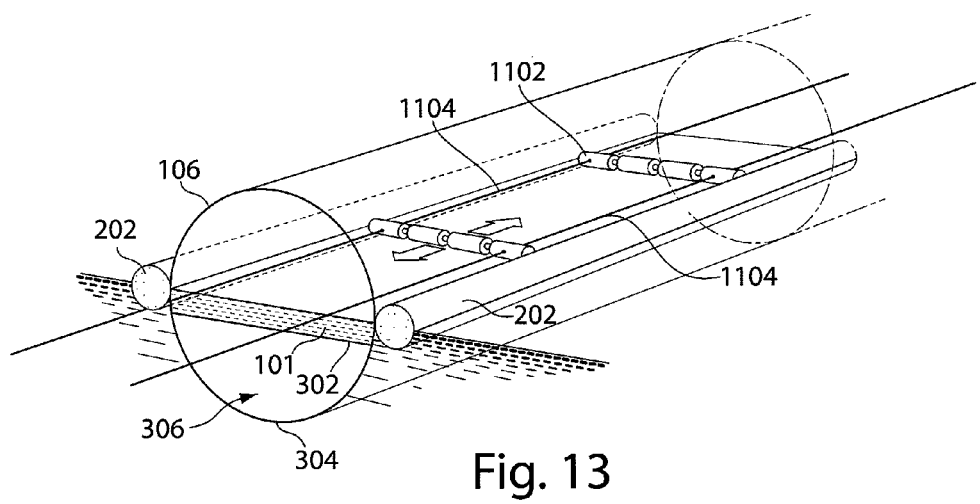
FIG. 13 is a perspective view of a photobioreactor including a mixing system according to another embodiment of the invention.

Another embodiment of a mixing system is illustrated in FIG. 13 in combination with a photobioreactor section having a divider 302, a second lower barrier 304, and a second channel 306.

Figure 14:
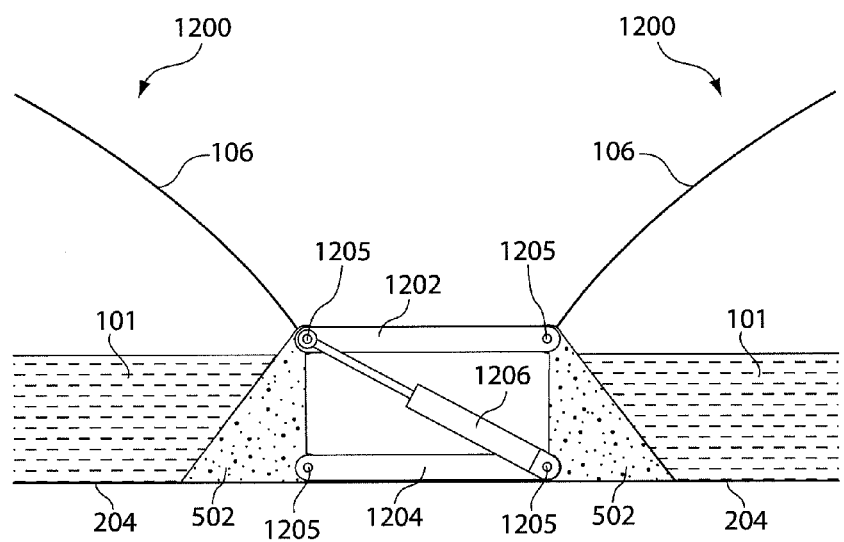
FIG. 14 is a cross-sectional view of a mixing system according to another embodiment of the invention.

In one embodiment, agitation of liquid medium 101 may be accomplished by rocking photobioreactor sections about a longitudinal axis of the photobioreactor sections. The rocking motion may be forced at a resonant frequency and may be performed using actuators connected to two photobioreactor sections interconnected in parallel. FIG. 14 illustrates one such embodiment including a pair of floating photobioreactor sections 1200 arranged side-by-side and connected periodically along the length of the photobioreactor units comprising the sections by rigid linkages such as an upper link 1202 and a lower link 1204. Linkages 1202, 1204 may be pivotally connected to edge supports 502 at pivot connections 1205. Some or all of the linkages may be driven by an actuator 1206, for instance a pneumatically, hydraulically, or electrically driven linear telescoping cylinder. The arrangement of linkages and cylinders permits a distributed alternating vertical displacement to be applied between the photobioreactor sections. In one embodiment, double-acting cylinders are used, allowing a neutral position as well as two forced positions of equal and opposite magnitude. Alternately driving the reactor edges up and down at the reactor resonant rolling frequency of the system induces mixing of the reactor contents and/or agitation of the liquid medium. Optimum frequency depends on reactor size and can be readily determined by those skilled in the art via routine experimentation but may be in the range of 0.2 to 2 Hz in some embodiments.

Agitation of liquid medium 101 also may be accomplished by horizontally moving photobioreactor sections. In some embodiments, the photobioreactor sections may be moved back and forth in directions substantially transverse to the longitudinal axis of the photobioreactor section. In still other embodiments, pitch and/or yaw rotations of photobioreactor sections (and/or roll rotations described above) may be used to agitate liquid medium 101.

In some embodiments, mixing and/or agitation may be provided by one or more paddlewheels, pumped jets of liquid, sparging of air or flue gas (see description of FIG. 17 below), induced wave propagation in the body of water on which the photobioreactor floats, or transverse or lengthwise periodic or episodic motion of the photobioreactor structure. Texture or other physical features may be added to the inner surfaces of the photobioreactor section(s) (e.g. to the top surface of the lower barrier and/or the submerged portions of the sidewalls) to increase turbulence and enhance mixing in the liquid medium. In certain embodiments, flow and/or mixing may be induced by continuously adding and withdrawing liquid medium to create a liquid head driving force. For example, continuously adding liquid medium to a first longitudinal end of a photobioreactor unit may induce flow toward the opposite longitudinal end of the photobioreactor unit. The rate of addition (and/or withdrawal) of liquid medium may be selected based at least in part on the ability of the lower barrier to resist movement in the areas of changing head.

Systems and methods disclosed herein may include monitoring and controlling mixing of the liquid medium within the photobioreactor to create desired or optimal exposure of the photosynthetic organisms to light based on measured light levels. Certain embodiments of the present invention provide systems include a control system which receives information from one or more light level sensors, and adjusts liquid medium mixing levels based on this information. for monitoring and/or controlling mixing of the liquid medium. The control system may include a computer-implemented system that is configured to control various operating parameters as well as to control flow within the photobioreactor to provide desired or optimal levels of mixing.

Achievable growth rates for known algal cultures are generally in the range of 10-150 grams per square meter of photobioreactor footprint per day. Given that the carbon dioxide output of a large power plant is typically in the thousands of tons per day, photobioreactor systems covering a large area may be needed to effectively process power plant emissions.

To construct such large scale photobioreactor systems, individual photobioreactor sections may be interconnected in series and/or parallel to achieve scale-up. For example, a photobioreactor unit of a photobioreactor system may be formed by connecting multiple photobioreactor sections defined by separate cover sections 106 in series. In this manner, constructing the designed length of the photobioreactor unit may be achieved simply by selecting and interconnecting the appropriate number of photobioreactor sections. In some embodiments, the length of photobioreactor unit may be changed and the rate of gas and/or liquid flow may be changed to accommodate long-term changes in treatment needs. Additionally, retrofitting the photobioreactor unit such as by increasing or decreasing the length may be possible. Further increases in scale can be achieved by interconnecting two or more photobioreactor units in parallel, as shown in FIG. 15 and described below.

Figure 15:
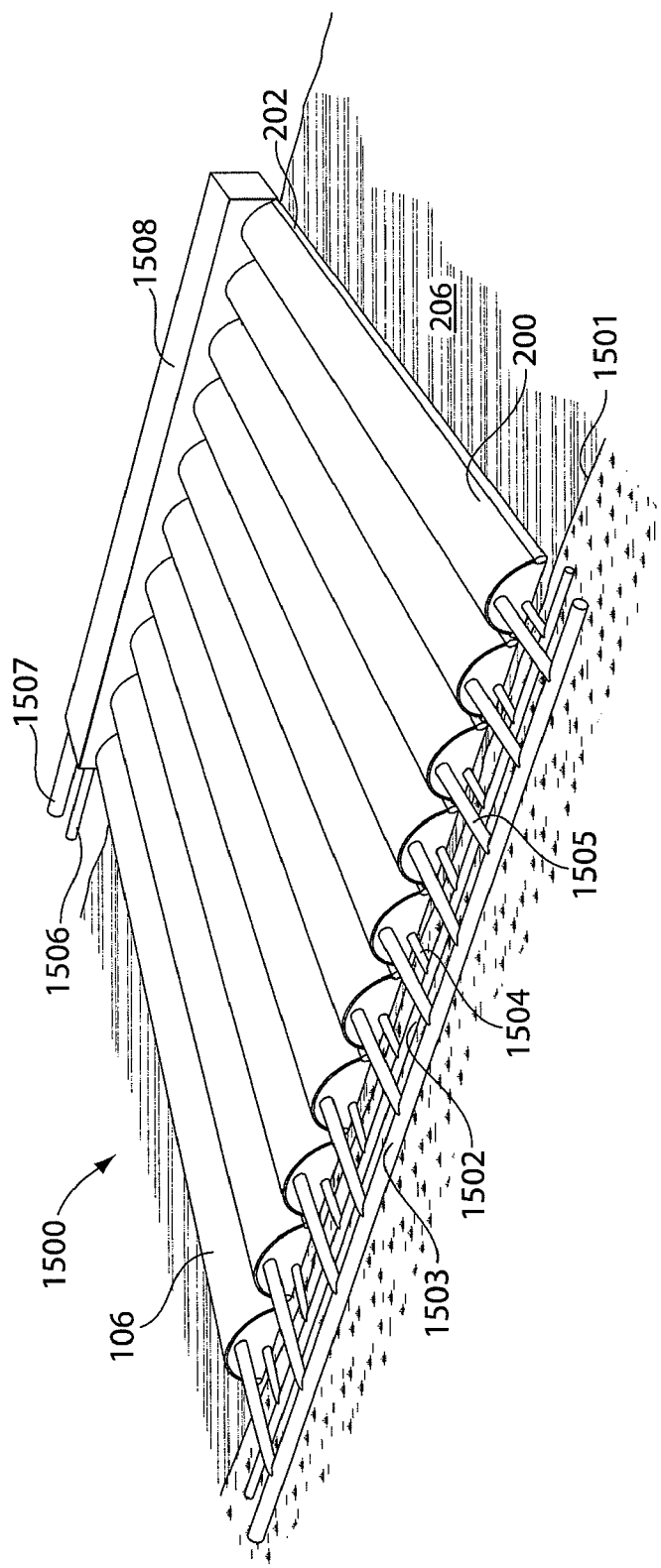
FIG. 15 is a perspective view of a photobioreactor system including a plurality of parallel photobioreactors.

Referring now to FIG. 15, one embodiment of a large-scale photobioreactor system 1500 is shown in perspective view. In this embodiment, the gas flows in the direction opposite to the liquid stream flow, however, in some embodiments, the gas may flow in the same direction as the liquid stream flow. Ten parallel photobioreactor units 200—each comprising a single photobioreactor section in the illustrated embodiment—are shown, but fewer (including a single photobioreactor unit) or more photobioreactor units may be used, and, in certain embodiments, at least one, some, or all of the photobioreactor units could comprise multiple, serially interconnected photobioreactor sections. While photobioreactor units 200 as illustrated comprise substantially straight, substantially linear sections, in alternative embodiments, one or more of the photobioreactor units may be arcuate, serpentine, or otherwise non-linear, if desired. A liquid inlet conduit 1502 and a gas outlet conduit 1503 run perpendicular to the photobioreactor units at a first end of photobioreactor system 1500. The conduits 1502, 1503 may be positioned on land at an edge 1501 of a body of water, as illustrated in this embodiment, or may be positioned to float on the body of water. In this embodiment, each conduit 1502, 1503 is a cylindrical conduit, but any suitable structures for transporting the gas and liquid to and from the photobioreactor units may be used. Conduits 1502, 1503 are connected to the photobioreactor units 200 with flexible liquid conduits 1504 and flexible gas conduits 1505, for example reinforced rubber hose, reinforced vinyl hose, or any other suitable conduit. At an opposite end of photobioreactor system 1500, a liquid outlet conduit 1506 and a gas inlet conduit 1507 are housed within shelter 1508 which also runs substantially perpendicular to the photobioreactor units 200. The inlet and outlet conduits at either end of the photobioreactor units may be housed within a shelter. In some embodiments, the gas inlets and outlets and the liquid medium inlets and outlets all may be positioned at one end of the photobioreactor units 200, for example on the end closest to land. In such embodiments, each photobioreactor unit may comprise two parallel photobioreactor sub-units (not shown) connected at the end away from land such that the liquid medium and gas travel away from land along a first photobioreactor sub-unit and return to land along a second, parallel photobioreactor sub-unit.

For photobioreactor systems which include multiple photobioreactor units connected in parallel, neighboring photobioreactor units may share an edge support or floatation element 202. Instead of or in addition to arch elements or other tensioners being provided for each photobioreactor unit, in certain embodiments a distributed outward horizontal force may be applied at the outer edges of the array of photobioreactor units, thereby tensioning all of the photobioreactor units.

For each of the photobioreactors described herein, the lengths of photobioreactor sections/units are selected to be sufficient, for a given desired liquid medium volume and/or circulation rate, to provide sufficient gas-liquid contact time to provide a desired level of mass transfer between the gas and the liquid medium. Optimal contact time depends upon a variety of factors, especially the algal growth rate and carbon and nitrogen uptake rate as well as feed gas composition and flow rate and liquid medium flow rate. Scalability of the photobioreactor system as a whole may be achieved, for example, by simply by adding additional photobioreactor sections/units to the system, such as by adding photobioreactor units in a parallel relationship to existing photobioreactor units.

In certain embodiments, floating objects and/or devices configured to be partially submerged in the liquid medium (e.g. a paddle wheel) may be used to facilitate enhancement of gas-liquid interfacial area and mass transfer. In certain such embodiments, the objects may be transparent such that they also may act to allow penetration of light to greater depths within the media. In some embodiments, elements may be employed to produce surface ripples or even waves that travel laterally and/or longitudinally within the liquid medium to increase mass transfer between the gas and the liquid.

As would be apparent to those skilled in the art, particular configurations of the various photobioreactor sections and photobioreactor units and components of the photobioreactor system will depend upon the particular use to which the photobioreactor is employed, the composition and quantity of the gas to be treated and other particular parameters specific to individual applications. Given the guidance provided herein and the knowledge and information available to those skilled in the arts of chemical engineering, biochemical engineering, and bioreactor design, one skilled in the art can select certain operating parameters and design configurations appropriate for a particular application, utilizing no more than a level of routine engineering and experimentation entailing no undue burden.

As discussed above, in certain embodiments, a photobioreactor system can comprise a plurality of identical or similar photobioreactor units interconnected in parallel. Furthermore, in certain embodiments, at least one or each photobioreactor unit may comprise one photobioreactor section or a plurality of photobioreactor sections interconnected in series. Such scalability can provide flexibility to increase the capacity of the photobioreactor system and/or increase the degree of removal of particular components of the gas stream as a particular application or need demands. In one such embodiment, a photobioreactor system is designed to separate algae species that are efficient in utilizing $NO_x$ from species efficient in utilizing $CO_2$. For example, a nitrogen-efficient algae is placed in a first photobioreactor section or a first zone of a photobioreactor section and carbon-efficient algae is placed in a second photobioreactor section or in a second zone of the same photobioreactor section in series with the first zone. The flue gas enters the first photobioreactor section/zone and is scrubbed of nitrogen (from $NO_x$), then flows through the second photobioreactor section/zone and is scrubbed of carbon (from $CO_2$).

The term "fluidically interconnected" or "interconnected," when used in the context of conduits, channels, chambers, photobioreactor sections or other structures provided herein that are able to contain and/or transport gas and/or liquid, refers to such conduits, channels, containers, reactors, or other structures being connected together, either directly or indirectly, so as to provide a continuous coherent flow path from one conduit or channel, etc. to the other(s) to which they are fluidically interconnected. In this context, two conduits or channels, etc. can be "fluidically interconnected" if there is, or can be established, liquid and/or gas flow through and between the conduits and/or channels (i.e. two conduits/channels are "fluidically interconnected" even if there exists a valve between the two conduits/channels that can be closed, when desired, to impede fluid flow there between).

Figure 16:
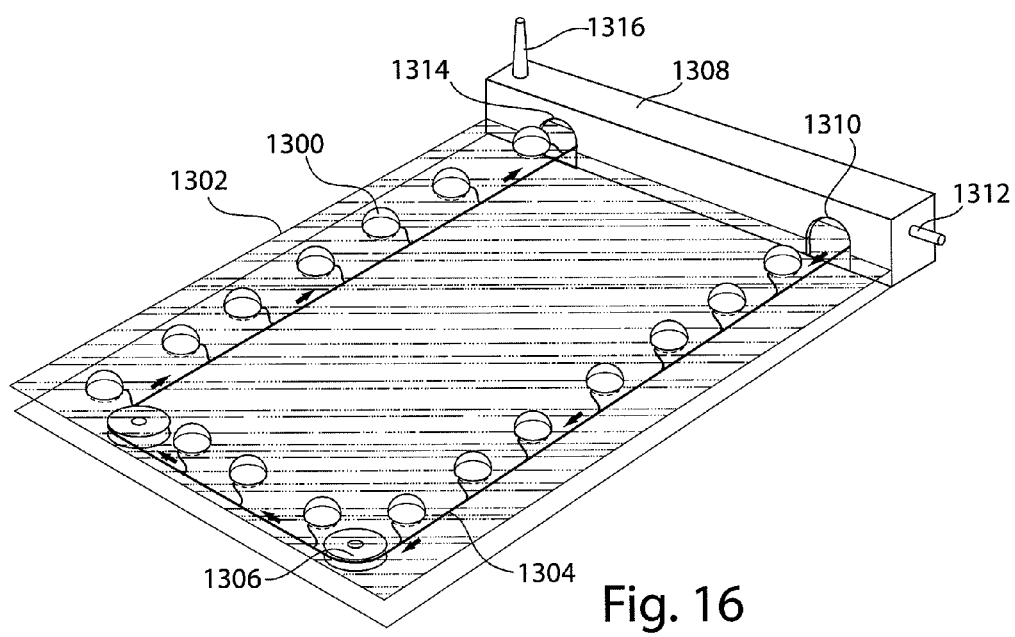
FIG. 16 is a perspective view of a conveyance system for a plurality of photobioreactors, according to one embodiment of the invention.

FIG. 16 is a schematic illustration of one embodiment of a photobioreactor system comprising a plurality of non-interconnected, sealed photobioreactor units. In the illustrated embodiment, floating, sealed photobioreactor units 1300 (e.g. sealed bag- or tube-like reactors as previously described) are conveyed on a predetermined path about the surface of a body of water 1302 by a cable 1304 and a cable drive system 1306, which may be submerged below or suspended above the surface of the body of water. A single loop passing across and back across the body of water is depicted in the schematic illustration; in practice multiple loops/passes may be utilized to achieve the desired residence time and area coverage. A photobioreactor unit processing facility 1308 supplies fresh liquid medium and pollutant gas (such as carbon dioxide-enriched gas) to photobioreactor units such as bags. The pollutant gas may come from a flue gas inlet 1312. The photobioreactor units are sealed and then sent to the body of water 1302 via photobioreactor unit outlet 1310. The photobioreactor units return to processing facility 1308 at photobioreactor unit inlet 1314, the units are unsealed, and the spent gas and liquid medium are removed. The units are then refilled, sealed, and sent back out via photobioreactor unit outlet 1310. Spent gas may be sent up a stack 1316. The removed liquid medium is further processed to harvest biomass to use as or convert into fuel or other products.

Any suitable method of adding and removing gas and liquid to and from the photobioreactor units may be employed. In some embodiments, a valve (e.g., a butterfly valve) may be used to selectively seal and unseal the photobioreactor units to provide an inlet/outlet. In other arrangements, an open end of a photobioreactor unit may be folded over itself and held closed with one or more clasps. In still other embodiments, an arrangement similar to a re-sealable zipper storage bag may be used.

In various embodiments described herein, carbon dioxide may be added to liquid medium in a dissolved carbonate/bicarbonate form instead of, or in addition to, providing a carbon dioxide-enriched gas headspace above the liquid medium and/or sparging carbon dioxide enriched gas into the liquid medium. In embodiments where carbon dioxide is added only through dissolved carbonate/bicarbonate, the dissolved concentration of carbon dioxide within the liquid medium may in certain cases be increased as compared to systems employing a gas headspace. Additionally, the filling and/or sealing of photobioreactor units such as flexible bags may be simplified in such embodiments, since operations would not require addition of gas or gas-tight connections.

Figure 17:
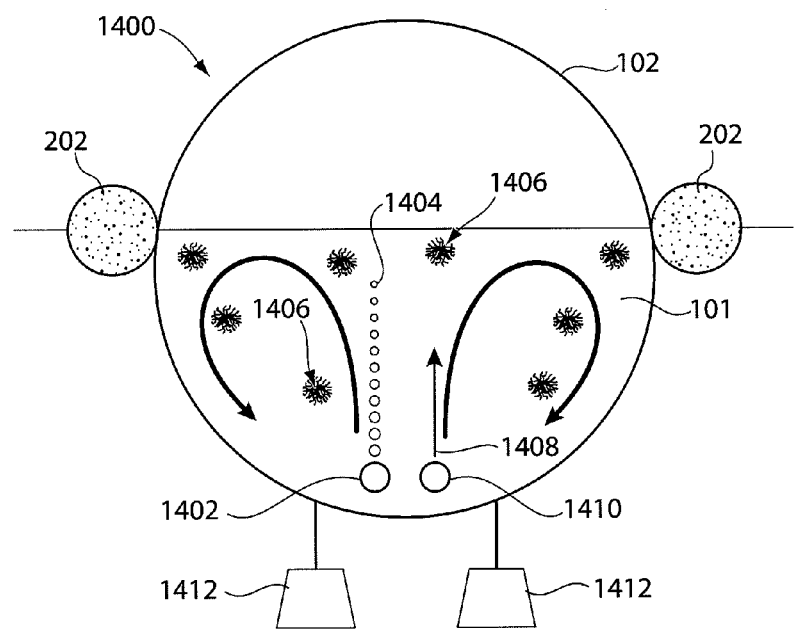
FIG. 17 is a cross-sectional view of a photobioreactor including a mixing system according to another embodiment of the invention.

In certain embodiments, macroalgae, for example seaweed, may be grown in various photobioreactors described herein. For certain embodiments in which macroalgae is the only or predominate species of phototrophic organism in culture, maintaining a substantially uniform medium depth and a substantially horizontal lower barrier orientation in the photobioreactor may be less important or even less desirable. An embodiment of a photobioreactor section that may be particularly suitable for culturing certain species of macroalgae is illustrated in FIG. 17. In some embodiments, the lower barrier 1401 may be curved or essentially semi-circular (as illustrated) and a gas sparger may be used to mix macroalgae 1406 in the liquid medium and/or introduce $CO_2$ enriched gas to the liquid medium. As shown in FIG. 17, a photobioreactor section 1400 may be formed from a tube 102 and may include floatation elements 202. A gas sparger 1402 may inject pressurized gas at or near the bottom of liquid medium 101, and gas bubbles 1404 serve to move and rotate macroalgae 1406 present in liquid medium 101. Rotation of macroalgae 1406 may help to expose the various sides of the macroalgae to direct sunlight, and movement of the macroalgae within liquid medium 101 may serve to alternate which pieces of macroalgae are at the top of liquid medium 101 and therefore receive the most sunlight. The curvature of lower barrier 1401 facilitates the circulation of liquid medium 101 by limiting "dead zones" where flow is reduced or non-existent. By providing a curved surface, less gas sparging may be needed to achieve a flow that substantially eliminates dead zones as compared to a photobioreactor section having a lower barrier with an essentially flat surface. Photobioreactor section 1400 also may include weights 1412 to maintain photobioreactor section 1400 and/or gas sparger 1402 in a substantially horizontal orientation. Weights 1412 and floatation elements 202 may be positioned at any suitable location on the photobioreactor section. Weights 1412 and/or floatation elements configured to maintain an orientation of gas sparger 1402 may be separate from weights and floatation elements that maintain an orientation of photobioreactor section 1400.

Instead of, or in addition to, sparging gas into liquid medium 101, a liquid stream 1408 may be injected into liquid medium 101 to induce circulation. In some embodiments, the liquid may be injected via one or more upwardly-facing water jets 1410. The liquid may be water, fresh liquid medium, re-circulated liquid medium drawn from tube 102, combinations of these and/or or any other suitable liquid.

The liquid medium contained within the photobioreactor system during operation typically comprises water or a saline solution (e.g. sea water or brackish water) containing sufficient nutrients to facilitate viability and growth of algae and/or other phototrophic organisms contained within the liquid medium. It is often advantageous to utilize a liquid medium comprising brackish water, sea water, or other non-portable water obtained from a locality in which the photobioreactor system will be operated and from which the algae contained therein was derived or is adapted to. Particular liquid medium compositions, nutrients, etc. required or suitable for use in maintaining a growing algae or other phototrophic organism culture are well known in the art. Potentially, a wide variety of liquid media can be utilized in various forms for various embodiments of the present invention, as would be understood by those of ordinary skill in the art. Potentially appropriate liquid medium components and nutrients are, for example, discussed in detail in: Rogers, L. J. and Gallon J. R. "Biochemistry of the Algae and Cyanobacteria," Clarendon Press Oxford, 1988; Burlew, John S. "Algal Culture: From Laboratory to Pilot Plant." Carnegie Institution of Washington Publication 600. Wash., D.C., 1961; and Round, F. E. The Biology of the Algae. St Martin's Press, New York, 1965; (each incorporated herein by reference).

In certain embodiments, the temperature, velocity, residence time, depths and/or nutrient concentrations can be maintained at different levels/values to control for different factors and/or provide particular functionality. For example, it is possible in certain embodiments to maintain conditions so as to enhance growth rates and in other embodiments to maintain conditions to enhance lipids production. For example, as described in commonly-owned U.S. patent application Ser. No. 11/818,962 and International Patent Application Publication No. WO 2008/008262, both incorporated herein by reference in their entireties, selective use of phosphate and/or nitrate can be used to influence growth rates and lipids production. Commonly-owned U.S. Published Patent Application No. US-2008-0009055 and PCT Publication No. WO 2008/008263 are also hereby incorporated by reference in their entireties.

Algae-rich liquid exiting from photobioreactor systems disclosed herein may be sent to a dewatering system. Various conventional methods and/or systems of dewatering may be used to dewater the algae, including dissolved air floatation and/or tangential flow filtration, or any other suitable dewatering approach.

The dewatered algae may be sent for further processing, for example, drying. Dried algal biomass can be used directly as a solid fuel for use in a combustion device or facility and/or could be converted into a fuel grade oil (e.g., biodiesel) and/or other fuel (e.g., ethanol, methane, hydrogen). The algae also may be used as food supplements for humans and animals. In certain embodiments, at least a portion of the biomass, either dried or before drying, can be utilized for the production of products comprising organic molecules, such as fuel-grade oil (e.g. biodiesel) and/or organic polymers. Methods of producing fuel grade oils and gases from algal biomass are known in the art (e.g., see, Dote, Yutaka, "Recovery of liquid fuel from hydrocarbon rich micro algae by thermo chemical liquefaction," Fuel. 73:Number 12. (1994); Ben-Zion Ginzburg, "Liquid Fuel (Oil) From Halophilic Algae: A renewable Source of Non-Polluting Energy, Renewable Energy," Vol. 3, No 2/3. pp. 249-252, (1993); Benemann, John R. and Oswald, William J., "Final report to the DOE: System and Economic Analysis of Micro algae Ponds for Conversion of $CO_2$ to Biomass." DOE/PC/93204-T5, March 1996; and Sheehan et al., 1998.

Algae-depleted medium resulting from dewatering operations may be disposed of or may be returned to photobioreactor system (after optionally being mixed with fresh liquid medium) to return unused nutrients to the system. Such an approach may reduce the amount of fresh water and nutrients to be added to the system.

In some embodiments, other processes of the photobioreactor system may be integrated with the power plant or other $CO_2$ source. For example, the hot flue gas from the power plant may be used to at least partially dry the biomass produced by the photobioreactor system. Further details regarding the processing of dewatered algae, the re-use of algae-depleted medium, and the integration of processes of the photobioreactor system with a power plant or other carbon dioxide source may be found in U.S. Published Application Nos. 2005/0260553, 2005/0064577, 2005/0239182, and International Publication No. WO2007/011343 A1, each of which is incorporated herein by reference in its entirety.

Algae, or other phototrophic organisms, may, in certain embodiments, be pre-adapted and/or pre-conditioned to specific environmental and operating conditions expected to be experienced in a full scale photobioreactor system of the invention during use. Methods and apparatus for adaptation and pre-conditioning algae may be found in commonly-owned International Application Publication No. WO 2006/020177, which is incorporated herein by reference in its entirety.

Although photobioreactor systems are described herein as being utilized with natural sunlight, in alternative embodiments, an artificial light source providing light at a wavelength able to drive photosynthesis may be utilized in supplement to or instead of natural sunlight. For example, a photobioreactor utilizing both sunlight and an artificial light source may be configured to utilize sunlight during the daylight hours and artificial light in the night hours, so as to increase the total amount of time in which the photobioreactor system can convert CO$_2$ to biomass through photosynthesis.

In some embodiments, an integrated system for performing an integrated combustion method may include a photobioreactor system wherein combustion gases are treated with the photobioreactor system to mitigate pollutants and to produce biomass, for example in the form of harvested algae which can be used as a fuel for the combustion device and/or for the production of other products, such as products comprising organic molecules (e.g. fuel grade oil (e.g. biodiesel) and/or organic polymers). Further description of such an integrated system, which can be used in conjunction with embodiments of photobioreactor systems disclosed herein, may be found in commonly-owned PCT Publication No. WO2006/020177 A1, published on Feb. 23, 2006, commonly-owned U.S. Patent Application Publication Nos. US-2005-0064577-A1 and US-2005-0239182-A1, and PCT Publication No. WO 2007/011343, each of which is hereby incorporated by reference in its entirety.

Example: Flexible Bag Photobioreactor Unit with Agitation

A flexible bag-like reactor was formed of two rectangular plastic films attached together along their edges. Three liters of a culture of microalgae (microalgae at a concentration of 1.3 grams/liter) was added to the reactor and a continuous flow of carbon dioxide-enriched air (CO$_2$ at 5% by volume) was supplied to the headspace above the culture. The reactor was floated on water, exposed to sunlight, and attached to a shaker that was running at 200 rpm. Growth rates of approximately 14-16 g/m$^2$/day were observed.

While several embodiments of the invention have been described and illustrated herein, those of ordinary skill in the art will readily envision a variety of other means and structures for performing the functions and/or obtaining the results or advantages described herein, and each of such variations, modifications and improvements is deemed to be within the scope of the present invention. More generally, those skilled in the art would readily appreciate that all parameters, dimensions, materials, and configurations described herein are meant to be exemplary and that actual parameters, dimensions, materials, and configurations will depend upon specific applications for which the teachings of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described. The present invention is directed to each individual feature, system, material and/or method described herein. In addition, any combination of two or more such features, systems, materials and/or methods, provided that such features, systems, materials and/or methods are not mutually inconsistent, is included within the scope of the present invention. In the claims (as well as in the specification above), all transitional phrases or phrases of inclusion, such as "comprising," "including," "carrying," "having," "containing," "composed of," "made of," "formed of," "involving" and the like shall be interpreted to be open-ended, i.e. to mean "including but not limited to" and, therefore, encompassing the items listed thereafter and equivalents thereof as well as additional items. Only the transitional phrases or phrases of inclusion "consisting of" and "consisting essentially of" are to be interpreted as closed or semi-closed phrases, respectively. The indefinite articles "a" and "an," as used herein in the specification and in the claims, unless clearly indicated to the contrary, should be understood to mean "at least one."

In cases where the present specification and a document incorporated by reference and/or referred to herein include conflicting disclosure, and/or inconsistent use of terminology, and/or the incorporated/referenced documents use or define terms differently than they are used or defined in the present specification, the present specification shall control.

What is claimed is:

1. An enclosed photobioreactor configured to float on a body of water, the photobioreactor comprising:
    an elongated, longitudinally-oriented photobioreactor section constructed and arranged to contain a liquid medium comprising phototrophic organisms therein, the photobioreactor section comprising:
    a substantially flexible lower barrier comprising an upper surface in contact with and supporting the liquid medium;
    a cover constructed and arranged to cover the liquid medium within the photobioreactor section and further constructed and arranged to provide a gas headspace under the cover and above the liquid medium, the cover being at least partially transparent to light of a wavelength capable of driving photosynthesis;
    a first floatation element disposed on a first lateral side of the photobioreactor section;
    a second floatation element disposed on a second lateral side of the photobioreactor section;
    the first and second floatation elements being constructed and arranged to support the photobioreactor section for floatation on the body of water; and
    a plurality of tensioners constructed and arranged to apply tension to the lower barrier so as to maintain a substantial portion of the area of the lower barrier in a substantially horizontal configuration when the photobioreactor section is charged with the liquid medium, such that a continuous layer of the liquid medium has a substantially uniform depth which extends from approximately the first floatation element to approximately the second floatation element over at least a portion of the area of the lower barrier.

2. A photobioreactor as in claim 1, wherein the lower barrier comprises a flexible barrier material supported by a support layer, and the tensioners apply tension to the support layer which in turn supports the flexible barrier material.

3. A photobioreactor as in claim 1, wherein the tensioners comprise a plurality of arcuate members, each of which is connected to the first and second lateral floatation elements, the arcuate members urging the first and second lateral floatation elements away from one another.

4. A photobioreactor as in claim 3, wherein the arcuate members additionally at least partially support the cover.

5. A photobioreactor as in claim 1, wherein the tensioners comprise a plurality of bobber/sink pairs attached to the lower barrier.

6. A photobioreactor as in claim 1, wherein at least a portion of the cover is constructed of a flexible material.

7. A photobioreactor as in claim 1, wherein the cover is integrally formed with the lower barrier.

8. A photobioreactor as in claim 1, wherein the cover is at least partially supported by gas pressure within the gas headspace that is greater than atmospheric air pressure.

9. A photobioreactor as in claim 1, wherein the gas headspace is fluidically connected to a source of carbon dioxide-enriched gas.

10. A photobioreactor as in claim 1, wherein the photobioreactor section is configured to maintain the continuous layer of the liquid medium at a depth of no more than 20 cm.

11. A photobioreactor as in claim 1, wherein the photobioreactor section is configured to maintain the continuous layer of the liquid medium at a depth of no more than 10 cm.

12. A photobioreactor as in claim 1, wherein the photobioreactor section is configured to maintain the continuous layer of the liquid medium at a depth of no more than 5 cm.

13. An enclosed photobioreactor configured to float on a body of water, the photobioreactor comprising:
an elongated, longitudinally-oriented photobioreactor section constructed and arranged to contain a liquid medium comprising phototrophic organisms therein, the photobioreactor section comprising:
a substantially flexible lower barrier comprising an upper surface in contact with and supporting the liquid medium;
a cover constructed and arranged to cover the liquid medium within the photobioreactor section and further constructed and arranged to provide a gas headspace under the cover and above the liquid medium, the cover being at least partially transparent to light of a wavelength capable of driving photosynthesis, and the gas headspace being fluidically connected to a source of carbon dioxide-enriched gas;
a first floatation element disposed on a first lateral side of the photobioreactor section;
a second floatation element disposed on a second lateral side of the photobioreactor section;
the first and second floatation elements being constructed and arranged to support the photobioreactor section for flotation on the body of water;
and a plurality of floats positioned between the first and second floatation elements, the floats being constructed and arranged to float in the liquid medium and support the lower barrier so as to maintain a substantial area of the lower barrier in a substantially horizontal configuration when the photobioreactor section is charged with the liquid medium, such that a continuous layer of the liquid medium has a substantially uniform depth which extends from approximately the first floatation element to the second floatation element over at least a portion of the area of the lower barrier.

14. An enclosed photobioreactor configured to float on a water body, the photobioreactor comprising:
a photobioreactor section constructed and arranged to contain a liquid medium comprising phototrophic organisms therein, the photobioreactor section comprising:
a lower barrier comprising an upper surface in contact with and supporting the liquid medium;
a cover constructed and arranged to cover the liquid medium within the photobioreactor section and further constructed and arranged to provide a gas headspace under the cover and above the liquid medium, the cover being at least partially transparent to light of at least one wavelength capable of driving photosynthesis;
a mechanical mixing system comprising at least one mixing element, the mixing system constructed and arranged to move the mixing element such that the mixing element contacts and mixes the liquid medium.

15. An enclosed photobioreactor configured to float on a body of water, the photobioreactor comprising:
first and second photobioreactor sections constructed and arranged to contain a liquid medium comprising phototrophic organisms therein, each photobioreactor section comprising:
a substantially flexible lower barrier comprising an upper surface in contact with and supporting the liquid medium; and
a cover constructed and arranged to cover the liquid medium within the photobioreactor section and further constructed and arranged to provide a gas headspace under the cover and above the liquid medium such that gas exchange is permitted between gas in the gas headspace and the liquid medium, the cover being at least partially transparent to light of a wavelength capable of driving photosynthesis;
a first plurality of tensioners attached to a first lateral side of the first photobioreactor section and anchored to a solid surface that is external to the photobioreactor; and
a second plurality of tensioners attached to a first lateral side of the second photobioreactor section and anchored to a solid surface that is external to the photobioreactor;
wherein a second lateral side of the first photobioreactor section is adjacent and attached to a second lateral side of the second photobioreactor section; and
wherein the first and second pluralities of tensioning elements apply tension to the lower barriers of the first and second photobioreactor sections.

16. An enclosed photobioreactor configured to float on a water body, the photobioreactor comprising:
a photobioreactor section constructed and arranged to contain a liquid medium comprising phototrophic organisms therein, the photobioreactor section comprising:
a lower barrier comprising an upper surface in contact with and supporting the liquid medium;
a cover constructed and arranged to cover the liquid medium within the photobioreactor section and further constructed and arranged to provide a gas headspace under the cover and above the liquid medium, the cover being at least partially transparent to light of at least one wavelength capable of driving photosynthesis; and
a selectively deployable divider configured to substantially fluidically isolate a first region of the photobioreactor section from a second region of the photobioreactor section, when the divider is deployed.

17. A photobioreactor system comprising:
a plurality of separate, sealed photobioreactor units floating on a body of water, each photobioreactor unit containing a liquid medium comprising at least one species of phototrophic organisms therein; and
a conveyor system configured to move the plurality of sealed photobioreactors around the body of water.

* * * * *